United States Patent [19]

Troutner et al.

[11] Patent Number: 5,395,608
[45] Date of Patent: * Mar. 7, 1995

[54] TRIAMINE CHELANTS, THEIR DERIVATIVES, COMPLEXES AND CONJUGATES

[75] Inventors: David E. Troutner, Phoenixville, Pa.; Christy S. John, Gaithersburg, Md.; Maroor R. A. Pillai, Vashi, India

[73] Assignee: The Curators of the University of Missouri, Columbia, Mo.

[*] Notice: The portion of the term of this patent subsequent to Mar. 31, 2009 has been disclaimed.

[21] Appl. No.: 697,861

[22] Filed: May 9, 1991

Related U.S. Application Data

[63] Continuation-in-part of Ser. No. 343,472, Apr. 26, 1989, Pat. No. 5,101,041.

[51] Int. Cl.$^6$ .................. A61K 49/00; A61K 35/14; C07C 211/00
[52] U.S. Cl. .................. 424/1.49; 424/1.69; 534/10; 534/14; 530/391.5; 564/368
[58] Field of Search .................. 424/1.1, 85.8, 1.65, 424/1.49, 1.69; 534/10, 14, 15, 729, 16; 548/518, 549; 546/256, 264, 265; 558/17; 562/437; 564/18, 34, 157, 212, 253, 367, 368; 530/391.5

[56] References Cited

U.S. PATENT DOCUMENTS

| | | | |
|---|---|---|---|
| 5,099,069 | 3/1992 | Gansow et al. | 564/368 |
| 5,101,041 | 3/1992 | Troutner et al. | 548/518 |
| 5,208,324 | 5/1993 | Klaveness et al. | 534/16 |

OTHER PUBLICATIONS

D. E. Troutner et al., "Pentadentate amine phenol complexes of $^{99m}$Tc," Chem. Nucl. Med. 585–593 (1990).
M. R. A. Pillai et al., Bioconjugate Chem. 2, 191–197 (1990).
M. R. A. Pillai et al., J. Nucl. Med., Proceed. of 36th Annual Meeting, No. 430, p. 832 (1989).
G. H. Searle et al., Aust. J. Chem. 32, 519–36 (1979).
R. J. Motekaitis et al., Inorg. Chem. 23, (3), 275–283 (1984).
C. H. Paik et al., J. of Radioanal Chem. 157, (2), 553–564 (1980).
C. John et al., J. Nucl. Med. 29, 814–815 (1988).
M. W. Brechbiel et al., Inorg. Chem. 25, (16), 2772–2781 (1986).
A. W. Addison et al., Inorg. Chimica Acta 147, 61–64 (1988).
F. Refosco et al., J. Chem. Soc. Dalton Trans. 611–615 (1988).
E. Chiotellis et al., Nucl. Med. Biol. 15, (2), 215–223 (1988).
M. R. A. Pillai et al., J. Nucl Med., Proceed. of 36th Annual Meeting, No. 430, p. 832 (1989).
John et al., J Nucl Med, Proceed of 36th Annual Meeting, No. 306, pp. 814–815 (1989).
Motekaitis et al., Inorg Chem. 23, (3), 275–283 (1984).
F. Refosco et al., J Chem Soc. Dalton Trans., 611–615 (1988).

*Primary Examiner*—Richard D. Lovering
*Assistant Examiner*—Lara E. Chapman
*Attorney, Agent, or Firm*—Karen L. Kimble

[57] ABSTRACT

A group of functionalized triamine chelants and their derivatives that form complexes with radioactive metal ions are disclosed. The complexes can be covalently attached to a protein or an antibody or antibody fragment and used for therapeutic and/or diagnostic purposes. The chelants are of the formula:

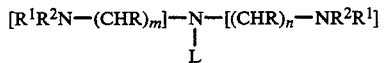

wherein n, m, R, $R^1$, $R^2$ and L are defined in the specification.

22 Claims, No Drawings

TRIAMINE CHELANTS, THEIR DERIVATIVES, COMPLEXES AND CONJUGATES

STATEMENT OF FEDERALLY SPONSORED RESEARCH

This invention was made with Government support under Grant No. DE-FG02-86ER60400 awarded by the Department of Energy. The Government has certain rights in this invention.

CROSS REFERENCES TO RELATED APPLICATION

The present application is a continuation-in-part application of U.S. application Ser. No. 343,472, filed Apr. 26, 1989, now U.S. Pat. No. 5,101,041, issued Mar. 31, 1992.

BACKGROUND OF THE DISCLOSURE

Functionalized chelants, or bifunctional coordinators, are known to be capable of being covalently attached to an antibody having specificity for cancer or tumor cell epitopes or antigens. Radionuclide complexes of such antibody/chelant conjugates are useful in diagnostic and/or therapeutic applications as a means of conveying the radionuclide to a cancer or tumor cell. See, for example, Meares et al., Anal. Biochem. 142, 68–78, (1984); M. W. Brechbiel et al., Inorg. Chem. 25(16), 2772–2781 (1986); and Krejcarek et al., Biochem. and Biophys. Res. Comm. 77, 581–585 (1977).

Numerous bifunctional chelating agents based on aminocarboxylic acids have been proposed and prepared. For example the cyclic dianhydride of DTPA [Hnatowich et al. Science 220, 613–615, (1983); U.S. Pat. No. 4,479,930] and mixed carboxycarbonic anhydrides of DTPA [Gansow, U.S. Pat. Nos. 4,454,106 and 4,472,509; Krejcarek et al., Biochem. and Biophys. Res. Comm. 77, 581–585, (1977)] have been reported.

Some chelating agents based on functionalized triamines are known. For example, G. H. Searle et al., Aust. J. Chem. 32, 519–36 (1979) teach for the protection of the terminal nitrogens of linear triamines which allows the central nitrogen atom to be functionalized with a methyl group. These compounds were used for the chelation of cobalt ions. When the terminal nitrogen atoms of linear triamines are functionalized with moieties capable of binding to metal ions using the general method disclosed by R. J. Motekaitis et al. [R. J. Motekaitis et al., Inorg. Chem. 23(3), 275–283 (1984)], then a pentadentate chelant is prepared. Additionally the central nitrogen atom is shown to be substituted with a benzyl group. These compounds were also used for the chelation of cobalt ions. A. W. Addison et al., Inorg. Chimica Acta 147, 61–64 (1988) and F. Refosco et al., J. Chem. Soc. Dalton Trans. 611–615 (1988) teach the preparation of a salicylaldehyde Schiff base ligand with a linear triamine in which the central nitrogen atom is functionalized with a methyl group. These compounds are used for the chelation of iron metal ions, and technetium and rhenium metal ions, respectively. E. Chiotellis et al., Nucl. Med. Biol. 15(2), 215–223 (1988) teach the preparation of linear triamines in which the terminal nitrogen atoms are functionalized with alkylthiol moieties. The central nitrogen atom is functionalized with a propyl or a cyclohexyl moiety. The compounds were used for complexation of $^{99m}$Tc.

Bifunctional chelating agents derived from triamines are also known. C. H. Paik et al., J. of Radioanal. Chem. 57(2), 553–564 (1980) teach a method to prepare functionalized terminal nitrogen atoms of linear triamines with moieties capable of binding to metal ions and having the central nitrogen atom substituted with a benzylamine group for conjugation to protein. These compounds were used for the chelation of $^{111}$In. Other linear triamine bifunctional chelating agents in which the central nitrogen atom is functionalized are disclosed by C. John et al. in J. Nucl. Med. 29, 814–815 (1988) in which the central nitrogen atom is functionalized with a benzylcarboxylic acid group. These compounds were used for the chelation of $^{105}$Rh and their conjugation with proteins and antibodies.

SUMMARY OF THE INVENTION

The invention includes the design and synthesis of novel bifunctional chelants, each containing a chelating functionality, and a chemically reactive group for covalent attachment to biomolecules. Also forming part of the invention are methods for preparing various BFC-metal complexes and the linking of the complexes to antibody to prepare radionuclide labeled antibody and/or fragments suitable for diagnostic and/or therapeutic applications.

The present invention is directed to novel bifunctional chelating agents (BFC) having a triamine functionality and derivatives thereof. The BFC's form complexes with "radioactive" metal ions. Preferred radioactive metal ions include $^{99m}$Tc, $^{105}$Rh, $^{109}$Pd, $^{57}$Co, $^{186}$Re, $^{188}$Re, $^{97}$Ru, $^{111}$In, $^{113m}$In, $^{67}$Ga, and $^{68}$Ga. The complexes so formed can be attached (covalently bonded) to an antibody or fragment thereof to form conjugates and used for therapeutic and/or diagnostic purposes. The complexes and/or conjugates can be formulated for in vivo or in vitro uses. A preferred use of the formulated conjugates is the treatment of cancer in animals, especially humans.

More specifically, the present invention is directed to a compound of the formula:

$$[R^1R^2N-(CHR)_m]-\underset{\underset{L}{|}}{N}-[(CHR)_n-NR^2R^1] \qquad (I)$$

wherein:

R represents independently hydrogen, $C_1$–$C_3$ alkyl, or benzyl;

$R^1$ represents $-CH_2C(CH_3)_2SH$, $-(CH_2)_2NH_2$, $-(CH_2)_2SH$,

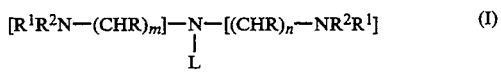

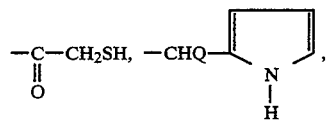

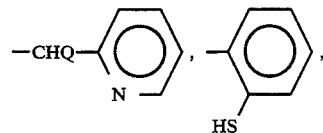

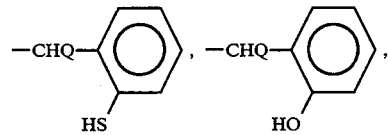

-continued

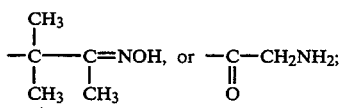

Q represents hydrogen, $C_1$–$C_3$ alkyl or phenyl;

$R^2$ represents hydrogen, —$CH_2CO_2H$, —$CH_2CH_2CO_2H$, or —$(CH_2)_2NH_2$;

m and n are independently 2, 3, or 4;

L is a linker/spacer group covalently bonded to, and replaces one hydrogen atom of the nitrogen atom to which it is joined, said linker/spacer group being represented by the formula

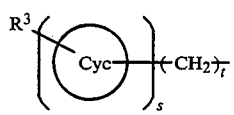

wherein:

s is an integer of 0 or 1;

t is an integer of 0 to 20 inclusive;

$R^3$ is an electrophilic or nucleophilic moiety which allows for covalent attachment to an antibody or fragment thereof, or a synthetic linker which can be attached to an antibody or fragment thereof; and Cyc represents a cyclic aliphatic moiety, aromatic moiety, aliphatic heterocyclic moiety, or aromatic heterocyclic moiety, each of said moieties optionally substituted with one or more groups which do not interfere with binding to an antibody or antibody fragment; or a pharmaceutically acceptable salt thereof.

Preferred features of the compounds of formula (I) are those where: R is hydrogen; $R^2$ is hydrogen; m and n are independently 2 or 3; and L is a compound of the formula:

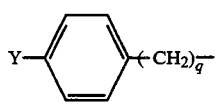

(A)

wherein:

Y is selected from the group consisting of nitro, amino, isothiocyanato, semicarbazido, thiosemicarbazido, carboxyl, bromoacetamido and maleimido;

q is 1, 2, or 3; or a pharmaceutically acceptable salt thereof.

When a conjugate of the present invention is desired Y must be other than nitro.

Preferred Compounds of formula (I) are those where m and n are 2 or 3, $R^2$ is hydrogen, $R^1$ is

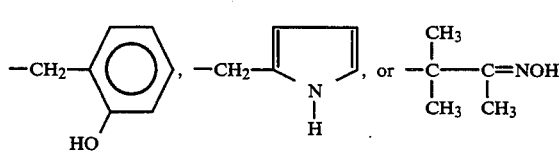

L is formula (A) where Y is amino or isothiocyanato, or a pharmaceutically acceptable salt thereof.

The present invention is also directed to radioactive metal ion complexes which have as their ligand the compounds of formula (I), especially radioactive metal ion complexes comprising $^{99m}Tc$, $^{105}Rh$, $^{109}Pd$, $^{57}Co$, $^{186}Re$, $^{188}Re$, $^{97}Ru$, $^{111}In$, $^{113m}In$, $^{67}Ga$, and $^{68}Ga$, with the with the proviso that when $R^2$ is —$CH_2CO_2H$ or —$CH_2CH_2CO_2H$, then the radioactive metal ion is selected from the group consisting of $^{186}Re$, $^{188}Re$, $^{99m}Tc$, $^{111}In$, $^{113m}In$, $^{67}Ga$, and $^{68}Ga$.

Additionally, the present invention concerns conjugates which are formed with the aforementioned complexes and antibody or antibody fragments.

In addition, the present invention also includes formulations having the conjugates of the invention and a pharmaceutically acceptable carrier, especially formulations where the pharmaceutically acceptable carrier is a liquid. The invention also includes a method for the diagnosis or treatment of a disease state, especially cancer, in a mammal which comprises administering to the mammal an effective amount of the formulation.

DETAILED DESCRIPTION OF THE INVENTION

As used herein, the following indicated terms have these meanings: with respect to the definition of Y, "electrophilic" moieties include, but are not limited to, isothiocyanate, bromoacetamide, maleimide, imidoester, thiophthalimide, N-hydroxysuccinimyl ester, pyridyl disulfide, and phenyl azide; suitable "nucleophilic" moieties include, but are not limited to, carboxyl, amino, acyl hydrazide, semicarbazide, and thiosemicarbazide; "synthetic linkers" include any synthetic organic or inorganic linkers which are capable of being covalently attached to an antibody or antibody fragment, preferred synthetic linkers are biodegradable synthetic linkers which are stable in the serum of a patient but which have a potential for enzymatic cleavage within an organ of clearance for the radioisotope, for example biodegradable peptides or peptide containing groups. Of the electrophilic moieties isothiocyanate is preferred and of the nucleophilic moieties amino, carboxyl, semicarbazide and thiosemicarbazide are preferred. It is desirable that the nature and/or position of Y be such that it does not appreciably interfere with the chelation reaction.

As used herein, the term "mammal" means animals that nourish their young with milk secreted by mammary glands, preferably warm blooded mammals, more preferably humans. "Antibody" refers to any polyclonal, monoclonal, chimeric antibody or heteroantibody, preferably a monoclonal antibody; "antibody fragment" includes Fab fragments and F(ab')$_2$ fragments, and any portion of an antibody having specificity toward a desired epitope or epitopes. When using the term "metal chelate/antibody conjugate" or "conjugate", the "antibody" portion is meant to include whole antibodies and/or antibody fragments, including semi-synthetic or genetically engineered variants thereof.

As used herein, "complex" refers to a compound of the invention, e.g. formula (I), complexed with a radioactive metal ion, wherein at least one metal atom is chelated or sequestered; "radioactive metal ion chelate/antibody conjugate" or "radioactive metal ion conjugate" refers to a radioactive metal ion conjugate that is covalently attached to an antibody or antibody fragment; "radioactive" when used in conjunction with the word "metal ion" refers to one or more isotopes of the elements that emit particles and/or photons, such as $^{99m}Tc$, $^{105}Rh$, $^{109}Pd$, $^{57}Co$, $^{186}Re$, $^{188}Re$, $^{97}Ru$, $^{111}In$, $^{113m}In$, $^{67}Ga$, and $^{68}Ga$; the terms "bifunctional coordinator", "bifunctional chelating agent" and "functionalized chelant" are used interchangeably and refer to compounds that have a chelant moiety capable of chelating a metal ion and a linker/spacer moiety covalently bonded to the chelant moiety that is capable of serving as a means to covalently attach to an antibody or antibody fragment.

As used herein, "pharmaceutically acceptable salt" means any salt of a compound of formula (I) which is sufficiently non-toxic to be useful in therapy or diagnosis of mammals. Thus, the salts are useful in accordance with this invention. Representative of those salts, which are formed by standard reactions, from both organic and inorganic sources include, for example, sulfuric, hydrochloric, phosphoric, acetic, succinic, citric, lactic, maleic, fumaric, palmitic, cholic, palmoic, mucic, glutamic, d-camphoric, glutaric, glycolic, phthalic, tartaric, formic, lauric, steric, salicylic, methanesulfonic, benzenesulfonic, sorbic, picric, benzoic, cinnamic acids and other suitable acids. Also included are salts formed by standard reactions from both organic and inorganic sources such as ammonium, alkali metal ions, alkaline earth metal ions, and other similar ions. Particularly preferred are the salts of the compounds of formula (I) where the salt is potassium, sodium, ammonium, H+ or mixtures thereof.

The bifunctional chelating agents described herein can be used to chelate or sequester the radioactive metal ions, so as to form metal ion chelates (also referred to herein as "complexes"). The complexes, because of the presence of the functionalizing moiety [represented by "Y" in formula (I)], can be attached to functionalized supports, such as functionalized polymeric supports, or preferably covalently attached to proteins or more specifically to antibodies or antibody fragments. Thus the complexes described herein complexed with radioactive metal ions may be covalently attached to a protein or an antibody or antibody fragment and are referred to herein as "conjugates". For example, human serum albumin (HSA), purchased from Sigma, was used to form conjugates with a protein.

The antibodies or antibody fragments which may be used in the conjugates described herein can be prepared by techniques well known in the art. Highly specific monoclonal antibodies can be produced by hybridization techniques well known in the art, see for example, Kohler and Milstein [Nature 256, 495–497 (1975); and Eur. J. Immunol. 6, 511–519 (1976)]. Such antibodies normally have a highly specific reactivity. In the radioactive metal ion conjugates, antibodies directed against any desired antigen or hapten may be used. Preferably the antibodies which are used in the radioactive metal ion conjugates are monoclonal antibodies, or fragments thereof having high specificity for a desired epitope(s). Antibodies used in the present invention may be directed against, for example, tumors, bacteria, fungi, viruses, parasites, mycoplasma, differentiation and other cell membrane antigens, pathogen surface antigens, toxins, enzymes, allergens, drugs and any biologically active molecules. Some examples of antibodies or antibody fragments are B72.3 and IgG. [The hybridoma cell line B72.3 is deposited in the American Type Culture Collection (ATCC) having the accession number HB 8108. The IgG was purchased from Sigma.] A more complete list of antigens can be found in U.S. Pat. No. 4,193,983, which is incorporated herein by reference. The radioactive metal ion conjugates of the present invention are particularly preferred for the diagnosis and treatment of various cancers.

The conjugates of this invention, and in some instances the complexes, are employed as a formulation. The formulation comprises a compound of formula (I) with the antibody and/or radioactive metal ion and a physiologically acceptable carrier, excipient or vehicle therefor. Thus, the formulation may consist of a physiologically acceptable carrier with a complex (metal ion+ligand), conjugate (metal ion+ligand+antibody). The methods for preparing such formulations are well known. The formulation may be in the form of a suspension, injectable solution or other suitable formulation. Physiologically acceptable suspending media, with or without adjuvants, may be used.

The formulations of the present invention are in the solid or liquid form containing the active radionuclide complexed with the ligand. These formulations may be in kit form such that the two components (i.e. ligand and metal, complex and antibody) are mixed at the appropriate time prior to use. Whether premixed or as a kit, the formulations usually require a pharmaceutically acceptable carrier.

Injectable compositions of the present invention may be either in suspension or solution form. In the preparation of suitable formulations it will be recognized that, in general, the water solubility of the salt is greater than the free base. In solution form the complex (or when desired the separate components) is dissolved in a physiologically acceptable carrier. Such carriers comprise a suitable solvent, preservatives such as benzyl alcohol, if needed, and buffers. Useful solvents include, for example, water, aqueous alcohols, glycols, and phosphonate or carbonate esters. Such aqueous solutions contain no more than 50 percent of the organic solvent by volume.

Injectable suspensions are compositions of the present invention requiring a liquid suspending medium, with or without adjuvants, as a carrier. The suspending medium can be, for example, aqueous polyvinylpyrrolidone, inert oils such as vegetable oils or highly refined mineral oils, or aqueous carboxymethylcellulose. Suitable physiologically acceptable adjuvants, if necessary to keep the complex in suspension, may be chosen from among thickners such as carboxymethylcellulose, polyvinylpryrrolidone, gelatin, and the alginates. Many surfactants are also useful as suspending agents, for example, lecithin, alkylphenol, polyethylene oxide adducts, napthalenesulfonates, alkylbenzenesulfonates, and the polyoxyethylene sorbitan esters.

Many substances which effect the hydrophobicity, density, and surface tension of the liquid suspension medium can assist in making injectable suspensions in individual cases. For example, silicone antifoames, sorbitol, and sugars are all useful suspending agents.

An "effective amount" of the formulation is used for therapy. The dose will vary depending on the disease being treated. Although in vitro diagnostics can be performed with the formulations of this invention, in vivo diagnostics are also contemplated using formulations of this invention. The conjugates and formulations of this invention can also be used in radioimmunoguided surgery (RIGS); however, the metals which could be used for this purpose are $^{99m}$Tc, $^{111}$In, $^{113m}$In, $^{67}$Ga and $^{68}$Ga.

The present invention provides chelants, complexes, and antibody conjugates some of which are more stable, and/or have improved biodistribution, and/or have more rapid clearance from the body, than those known in the art.

DETAILED DESCRIPTION OF THE PROCESS

All of the starting materials required for preparing the compounds of this invention are either available from commercial sources or can be made from a known literature reference description.

The electrophilic moiety ("Y" in the formula) can also be prepared by methods known to the art. Such methods may be found in Acc. Chem. Res. 17, 202–209 (1984).

General methods of preparation for the compounds of formula (I) are well known in the art. Some of the various methods are shown in the following reaction schemes.

In the following Scheme I, the terminal amines of a symmetrical or unsymmetrical triamine are protected by the addition of phthalic anhydride using a modification of the procedure of G. H. Searle, et al., Aust. J. Chem. 32, 519–36 (1979). The central amine is then alkylated with the L moiety.

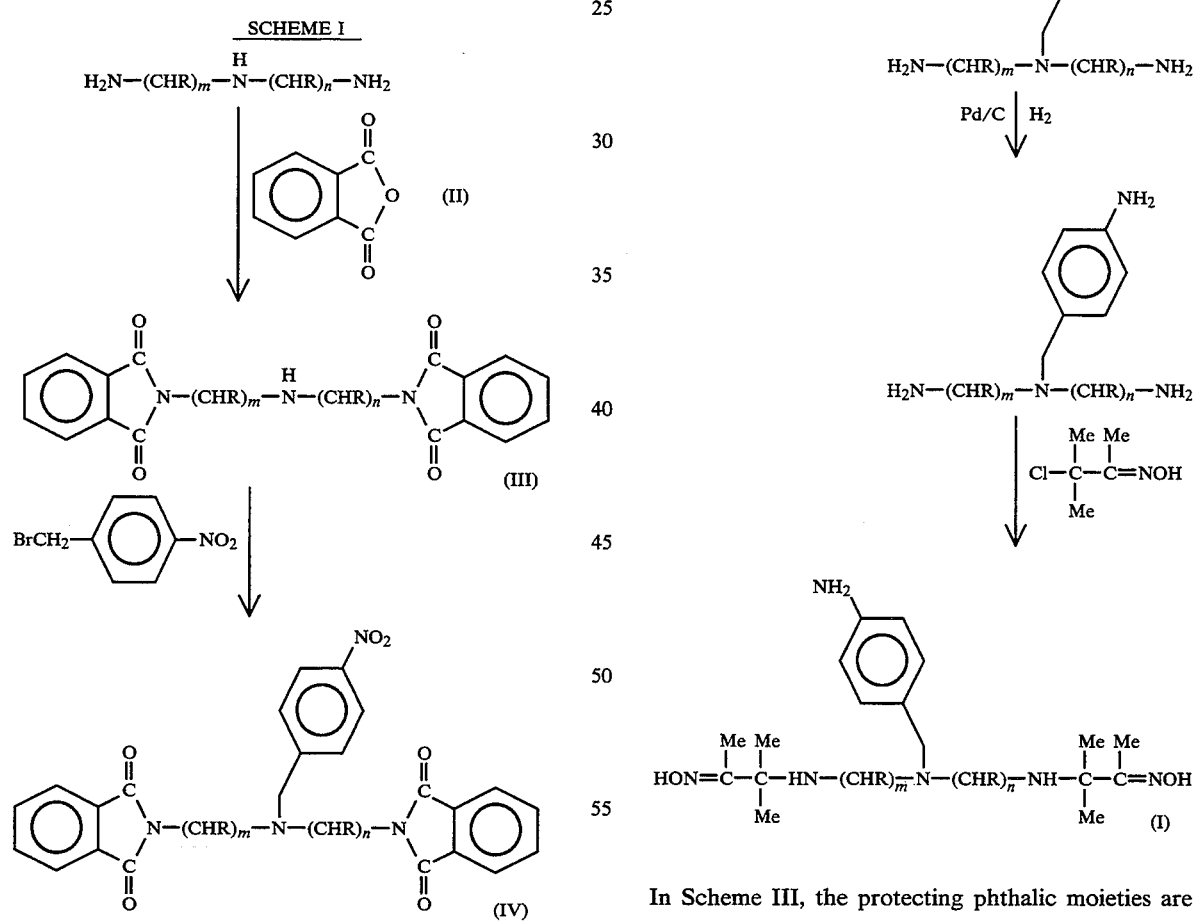

In Scheme II, the protecting phthalic moieties of the product from Scheme I are removed by hydrolysis with hydrochloric acid. The p-nitrobenzyl group is then reduced by conventional methods, i.e. Pd/C with $H_2$. The compounds of formula (I) where $R^1$ is an oxime are prepared by the addition of 3-chloro-3-methyl-2-butanone oxime.

In Scheme III, the protecting phthalic moieties are removed by hydrolysis with hydrochloric acid. The Schiff bases are then prepared by reaction with the appropriate aldehyde. Reduction of the Schiff bases proceeds with sodium borohydride. The nitro group is then reduced to the amine using Pd/C with $H_2$.

SCHEME III

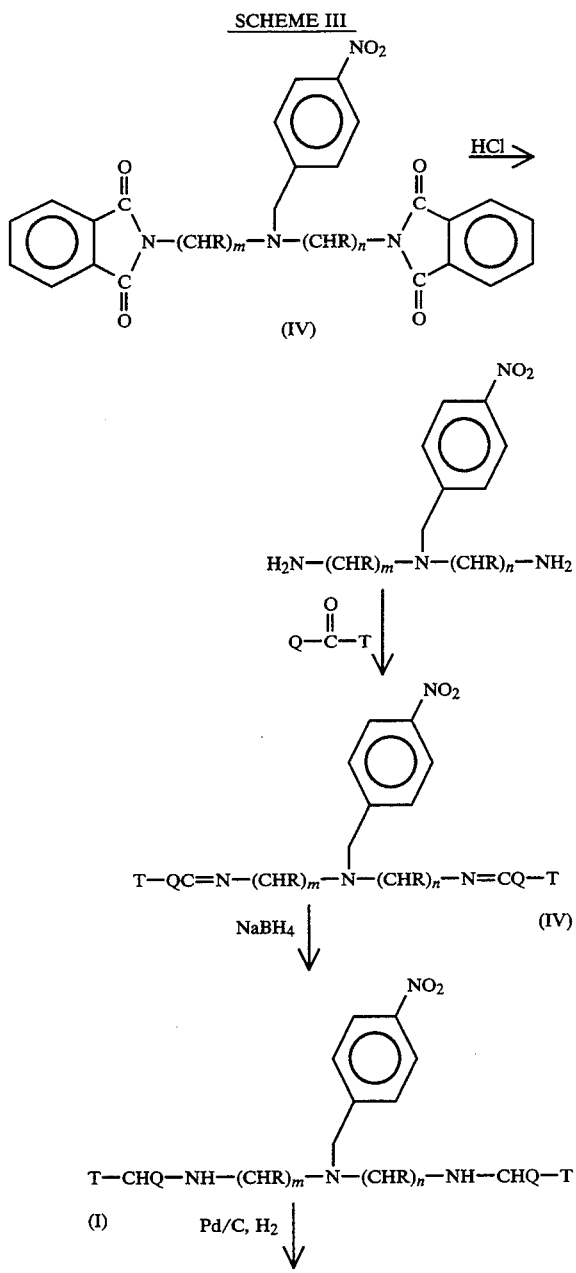

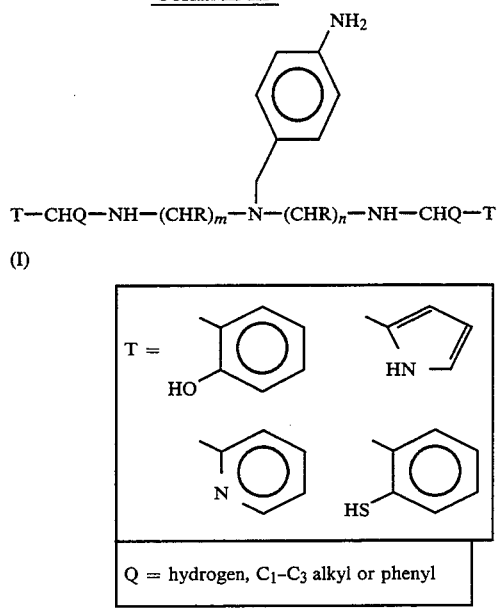

Q = hydrogen, $C_1$-$C_3$ alkyl or phenyl

In Scheme IV, the protecting phthalic moieties are removed by hydrolysis with hydrochloric acid. The compounds of formula (I) where Y is nitro and the $R^1$ groups are the correspondingly protected aminoamide or thioamide are then formed by reaction with the corresponding alkyl amino ester (e.g. methyl 2-(tBOC)-aminoacetate) or alkylthio ester (e.g. methyl 2-mercaptoacetate). When the tertiary butylcarbamate (tBOC) is present, it is cleaved by trifluoroacetic acid.

For compounds having either the unprotected aminoamide or thioamide moiety, the nitro group is then reduced to the amine using Pd/C with $H_2$.

Additionally, for compounds where Y is nitro having either the unprotected amino amide or thioamide moieties, reduction with borane leads to the corresponding alkyl amines or alkyl sulfhydryls. Subsequent reduction of the nitro group results in the corresponding amines.

SCHEME IV

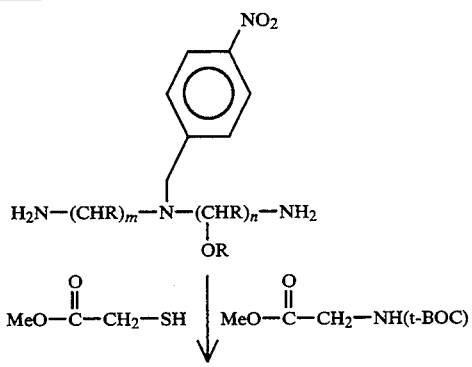

-continued
SCHEME IV
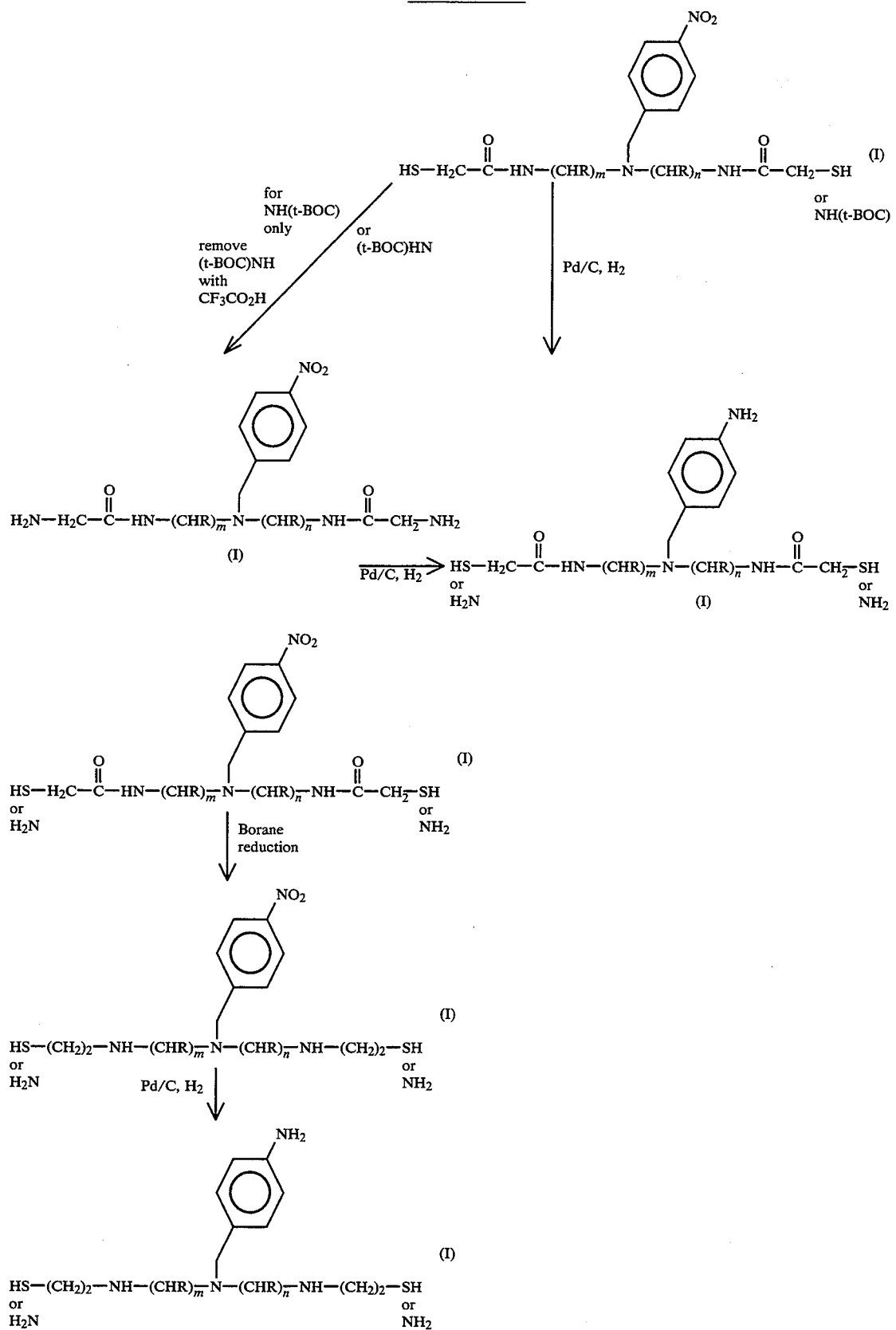
In Scheme V, to prepare the compounds of formula (I) where $R^2$ is other than hydrogen, the corresponding compounds of formula (I) where $R^2$ is hydrogen are reacted in one of the following manners.

The compounds of formula (I) wherein $R^2$ is alkyl amine are prepared by a modification of the Strecker reaction (aldehyde reaction with hydrogen cyanide, followed by reduction with lithium aluminum hydride).

The compounds of formula (I) wherein $R^2$ is a carboxylic acid are prepared by the addition of bromocarboxylic acid. See for example, J. F. Desreux, Inorg. Chem. 19, 1319-1324 (1980).

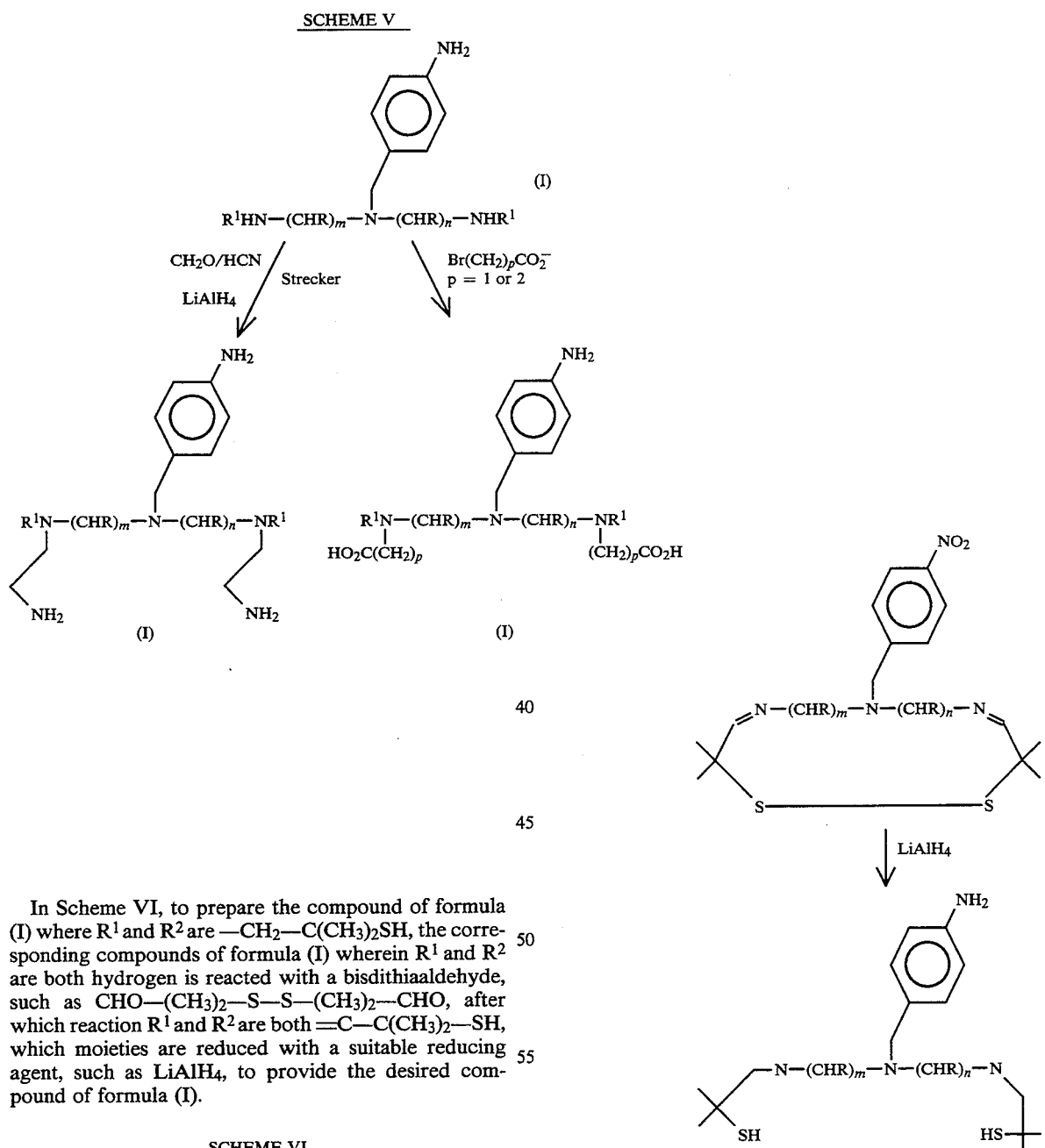

In Scheme VI, to prepare the compound of formula (I) where $R^1$ and $R^2$ are $-CH_2-C(CH_3)_2SH$, the corresponding compounds of formula (I) wherein $R^1$ and $R^2$ are both hydrogen is reacted with a bisdithiaaldehyde, such as $CHO-(CH_3)_2-S-S-(CH_3)_2-CHO$, after which reaction $R^1$ and $R^2$ are both $=C-C(CH_3)_2-SH$, which moieties are reduced with a suitable reducing agent, such as $LiAlH_4$, to provide the desired compound of formula (I).

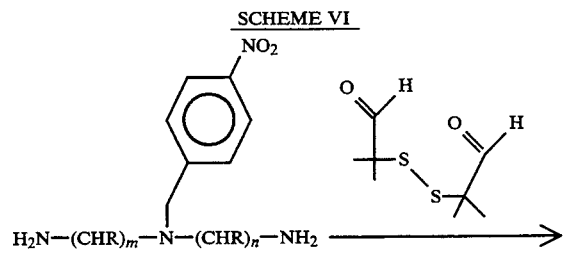

Radionuclides can be produced in several ways. For example, several preparations are detailed in an article by D. E. Troutner, Nucl. Med. Biol., 14(3), 171-176 (1987). The method of obtaining the nuclides employed in the present invention is not critical thereto.

The complexes of the present invention are generally prepared by mixing the ligand with the desired radioactive metal ion. However, when the radioactive metal ion is $^{186}$Re, $^{188}$Re or $^{99m}$Tc, then a reducing agent must be added such as tin tartarate. When the radioactive metal ion is $^{97}$Ru or $^{105}$Rh, then the mixture must be heated.

Attachment of radionuclide to antibody can be carried out by conjugation of the antibody to preformed (ambient or elevated temperature) metal—BFC complex. See European published application 0296522, published Dec. 28, 1988]. The conjugates of the present invention are prepared by first activating the complex with thiophosgene which converts the amine, where Y is NH$_2$, to the corresponding isothiocyanate. The desired protein or antibody or antibody fragment, in presence of buffer, is added to the isothiocyanate compound. A covalent bond is formed (thiourea) by the reaction of the isothiocyanate with the alkylamine of a lysine group.

The invention will be further clarified by a consideration of the following examples, which are intended to be purely exemplary of the use of the invention.

In the following examples, the following terms and conditions were used unless otherwise specified:

Room temperature means about 25° C.;

Bq means a Becquerel unit for measuring radioactivity. 1 Curie=3.7×10$^{10}$ Bq;

0.9% Saline solution was prepared by dissolving 9 g of NaCl in 1 L of doubly distilled water;

$^{105}$Rh was prepared at the University of Missouri Research Reactor (MURR) and supplied as Na$_3$(RhCl$_6$) or Na$_2$(RhCl$_5$.H$_2$O) in approximately pH 4 HCl solution;

Rh carrier solutions were prepared by dissolving RhCl$_3$.3H$_2$O in saline;

$^{99m}$Tc was eluted from a Mallinckrodt technetium generator and diluted to 2 mCi/mL using 0.9% saline solution;

Human immunoglobulin (I-4506) was purchased from Sigma Chemical Company;

Sephadex ™ G 75 was purchased from Sigma Chemical Company;

Anti-human IgG (γ chain specific), Agarose (A-6656) was purchased from Sigma Chemical Company;

Thiophosgene was purchased from Aldrich Chemical Company;

RhCl$_3$.3H$_2$O was purchased from Aldrich Chemical Company;

Flexible silica gel plates 7.5×2.5 cm, coating thickness 250 μm were purchased from J. T. Baker Chemical Company;

Beckman series 320046 paper (30×2 cm) was used for paper electrophoresis and Gelman Science solvent saturation pads cut into 1.5×13.7 cm were used for paper chromatography;

$^1$H and $^{13}$C NMR spectra were recorded on a JEOL FX-90Q spectrometer, 300 MHz with δ reported in ppm relative to TMS as an internal standard; and Radioactivity was measured on a standard 5×5 cm NaI (T1) well scintillation counter.

PREPARATION OF STARTING MATERIALS

EXAMPLE A

Method A: Preparation of 4-(4-nitrobenzyl)-1,7-diphthaloyldiethylenetriamine

To a round bottom flask was added 100 mL of absolute ethanol and 1.6 g (28 mmol) of potassium hydroxide. The resulting mixture was heated until the potassium hydroxide dissolved.

Ten g (28 mmol) of N,N'-(iminodiethylene)bisphthalimide [prepared by the procedure of G. H. Searle et al. Aust. J. Chem. 32, 519-36 (1979)(see page 531)] was added to the solution and then the reaction mixture was refluxed for 2.5 hours. To the mixture was added 5.95 g (28 mmol) of p-nitrobenzylbromide and the mixture was again refluxed for 16 hours. The solution was filtered hot and upon cooling the filtrate, the product crystallized, and was filtered to yield 11.0 g of 4-(4-nitrobenzyl)-1,7-diphthaloyldiethylenetriamine, mp 128°-130° C. The product was recrystallized from absolute ethanol and further characterized by: $^1$H NMR (CDCl$_3$) δ 2.6-2.9 (t, 4H), 3.6-3.9 (m, 6H), 7.1-7.6 (m, 12H).

Method B: Preparation of 4-(4-nitrophenyl)-1,7-diphthaloyldiethylenetriamine

To a round bottom flask was added 100 mL of absolute ethanol and 1.6 g (28 mmol) of potassium hydroxide. The resulting mixture was heated until the base dissolved. N,N'-(iminodiethylene)bisphthalimide, 10 g (28 mmol) [prepared by the procedure of Martell et al., Inorg. Chem. 18(11), 2982-2986 (1979)] was added to the solution and the reaction mixture refluxed for 2.5 hours. To the mixture was added 5.95 g (28 mmol) of p-nitrobenzyl bromide and the mixture was again refluxed for 16 hours. The solution was filtered hot and upon cooling the filtrate, the product crystalized and was filtered to yield 11 g of 4-(4-nitrobenzyl)-1,7-diphthaloyldiethylenetriamine, mp 130° C. The product was reerystalized from absolute ethanol and further characterized by: $^1$H NMR (CDCl$_3$) δ 2.6-2.9 (t, 4H), 3.6-3.9 (m, 6H), 7.1-7.6 (m, 12H).

EXAMPLE B

Preparation of 4-(p-nitrobenzyl)diethylenetriamine

To a round bottom flask was added 3.0 g of 4-(p-nitrobenzyl)-1,7-diphthaloyldiethylenetriamine (prepared in Example A) and 60 mL of 6M hydrochloric acid. The mixture was refluxed for about 16 hours. A clear solution was obtained, which upon cooling produced a white solid. The solid was filtered and the filtrate evaporated on a rotary evaporator to give as a white solid 1.9 g (91%) of 4-(p-nitrobenzyl)diethylenetriamine as the hydrochloride salt. This salt was neutralized with sodium hydroxide solution and extracted into chloroform (3 times with 30 mL portions). The organic layers were combined and evaporated to yield as an oil, 4-(p-nitrobenzyl)diethylenetriamine. $^1$H NMR (CDCl$_3$) δ 1.65 (s, 4H), 2.4-2.9 (m, 8H), 3.7 (s, 2H), 7.3-8.3 (m, 4H).

EXAMPLE C

Preparation of bis(salicylidine)-4-(p-nitrobenzyl)diethylenetriamine.

In 50 mL of ethanol in a round bottom flask was added 700 mg (2.4 mmol) of 4-(p-nitrobenzyl)diethylenetriamine (prepared in Example B) and 720 mg (5.9 mmol) of salicylaldehyde in 50 mL of ethanol. The mixture was refluxed for 18 hours. A bright yellow solution was formed. The solvent was removed by rotary evaporation, leaving an oil. The oil was crystallized from hot ethanol, yielding bis(salicylidine)-4-(p-nitrobenzyl)diethylenetriamine, mp 86°-88° C. and further characterized by: $^1$H NMR (CDCl$_3$) δ 2.8-3 (t, 4H), 3.6-3.9 (m, 6H), 6.8-8 (m, 12H), 8.2 (s, 2H). $^{13}$C NMR (CDCl$_3$) δ 8 55.27, 57.76, 58.68, 116.87, 118.55, 123.42, 128.90, 131.17, 132.20, 147.15, 160.97, 165.85.

EXAMPLE D

Preparation of 4-(p-aminobenzyl)diethylenetriamine

In 60 mL of absolute ethanol was dissolved 1 g of 4-(p-nitrobenzyl)diethylenetriamine (prepared in Example B) and 100 mg of palladium on activated charcoal (10% Pd) was added. The mixture was hydrogenated at 40 psi (275.8 kPa) for 24 hours. The catalyst was removed by filtration and the filtrate evaporated to give 0.9 g of product as an oil. The oil solidified upon cooling and the solid was crystallized from ethanol to provide 4-( p-aminobenzyl)-diethylenetriamine and further characterized by: $^1$H NMR (CDCl$_3$) δ 8 2.2–2.8 (m, 12H), 3.4 (s, 2H), 6.4–7.15 (m, 4H). $^{13}$C NMR (CDCl$_3$) δ 38.05, 55.54, 57.01, 113.34, 121.28, 128.42, 143.0.

EXAMPLE E

Preparation of 1,7-bis(pyrrolecarboxylidine)-4-(p-nitrobenzyl)diethylenetriamine.

(p-Nitrobenzyl)diethylenetriamine, 2 g (8.5 mmol), was dissolved in 150 mL of ethanol and 1.6 g (17 mmol) of (2-pyrrole)carboxaldehyde was added. The mixture was refluxed for 16 hours. The ethanol was evaporated. The product, 1,7-bis(pyrrolecarboxylidine)-4-(p-nitrobenzyl)-diethylenetriamine, was obtained as an oil.

The product, 1,7-bis(pyrrolecarboxylidine)-4-(p-nitrobenzyl)diethylenetriamine, was used without purification or characterization in the following examples.

EXAMPLE F

Preparation of α,α'-dithiodiisobutyraldehyde.

A modified procedure by Niederhauser (U.S. Pat. No. 2,580,695) was employed. To a stirred solution of 578 g (8.0 mol) of isobutyraldehyde in 920 g of carbon tetrachloride, was added dropwise at 40°–50° C. in 4 hours 540 g (4.0 mol) of 98% sulfur monochloride. Hydrogen chloride gas was copiously liberated and occasional cooling was necessary during the addition period. The stirred solution was held at 30°–40° C. for an additional 48 hours while a current of nitrogen was passed through the solution in order to remove the hydrogen chloride. The solution was distilled and an 80% yield of α,α'-dithiodiisobutyraldehyde was obtained and further characterized by: $^1$H NMR (CDCl$_3$) δ 1.40 (s, 12H), 9.09 (s, 2H).

EXAMPLE G

Preparation of 3,3,13,13-tetramethyl-1,2-dithia-5,8,11-triazatridecane-8-(p-nitrobenzyl)-5,11-diene.

To a stirred solution of 1.24 g (6.025 mmol) α,α'-dithiodiisobutyraldehyde (prepared in Example F) in 70 mL of anhydrous benzene was added dropwise 1 g (6.025 mmol) of 4-(p-nitrobenzyl)diethylenetriamine (prepared in Example B). The mixture was refluxed for 16 hours and the reaction monitored by thin layer chromatograhry (TLC) (ether/hexane, 1/1, v/v). After completion of the reaction, the solution was transferred to a separatory funnel and washed several times with water. The organic layer was dried over magnesium sulfate and the solvent evaporated. The Shiff base was obtained as a glassy residue and was used without further purification and characterized by: $^1$H NMR (CDCl$_3$) δ 1.5 (s, 12H), 2.8 (t, 4H), 3.48 (t, 4H), 3.78 (s, 2H), 7.6 (d, 2H), 8.2 (d, 2H); $^{13}$C NMR (CDCl$_3$) δ 26.09, 55.01, 58.78, 59.85, 123.52, 128.49, 129.09, 129.45, 168.15.

PREPARATION OF LIGAND FINAL PRODUCTS

EXAMPLE 1

Preparation of bis(2-hydroxybenzyl)-4-(p-nitrobenzyl)-diethylenetriamine.

In 70 mL of ethanol was dissolved 2.0 g (4.5 mmol) of bis(salicylidine)-4-(p-nitrobenzyl)diethylenetriamine (prepared in Example C). To the solution was added 0.3 g (8.1 mmol) of sodium borohydride. The reaction mixture was stirred for 2 hours at room temperature. A white solid precipitated, was filtered, and washed with aqueous ethanol. The product was recrystallized from absolute ethanol to provide bis(2-hydroxybenzyl)-4-(p-nitrobenzyl)diethylenetriamine, mp 108°–110° C. and further characterized by: $^1$H NMR (CDCl$_3$) δ 2.6 (s, 8H), 3.6 (s, 2H), 3.9 (s, 4H), 6.3 (b, 2H), 6.7–8.2 (m, 14H). $^{13}$C NMR (CDCl$_3$) δ 46.01, 52.45, 54.08, 58.85, 116.27, 118.98, 122.18, 123.69, 128.24, 128.73, 129.33, 146.61, 158.04.

EXAMPLE 2

Preparation of bis(2-hydroxybenzyl)-4-(p-aminobenzyl)diethylenetriamine.

In 40 mL of absolute ethanol was dissolved 400 mg of bis(2-hydroxybenzyl)-4-(p-nitrobenzyl)diethylenetriamine (prepared in Example 1) and 100 mg of palladium on activated charcoal (10% Pd). The mixture was hydrogenated at 40 psi (275.8 kPa) for 24 hours. The catalyst was removed by filtration. The ethanolic solution was evaporated to provide bis(2-hydroxybenzyl)-4-(p-aminobenzyl)diethylenetriamine, and was characterized by: $^1$H NMR (CDCl$_3$), carbon protons only; amine and hydroxyl protons were not included: δ 2.6 (s, 8H), 3.4 (s, 2H), 3.8 (s, 4H), 6.4–7.2 (m, 12H). $^{13}$C NMR (CDCl$_3$) δ 46.06, 52.35, 53.48, 58.74, 115.08, 116.33, 118.87, 122.50, 128.35, 128.62, 130.03, 145.74, 158.31.

EXAMPLE 3

Preparation of 3,3,11,11-tetramethyl-4,7,10-triazatridecane-7-(p-aminobenzyl)-2,12-dionedioxime.

To a dry flask was added 0.49 g (2.35 mmol) of 4-(p-aminobenzyl)diethylenetriamine and 100 mL of dry methanol. The solution was cooled at 0° C. To the solution was added 0.64 g (4.7 mmol) of 3-chloro-3-methyl-2-butanone oxime. The solution was stirred at 0° C. for 1.5 hours and then refluxed for 16 hours. After the mixture was cooled, the volatiles were removed by rotary evaporation. A yellow glassy solid was neutralized with Na$_2$CO$_3$ solution. The resulting gummy solid was extracted with two 100 mL portions of diethyl ether. The ether was removed by rotary evaporation. The product was loaded onto a silica gel column and eluted with chloroform. The third band eluted was taken as the product and gave as an oil, after extraction with chloroform and rotary evaporation, 3,3,11,11-tetramethyl-4,7,10-triazatridecane-7-(p-aminobenzyl)-2,12-dionedioxime, which was characterized by: $^1$H NMR (CDCl$_3$) δ 1.7 (s, 12 H), 1.9 (s, 6H), 3.1 (s, 6 H), 3.3 (s, 4H), 4.3 (s, 2H), 6.5–7.3 (m, 6H), 9.3 (b, 2H).

EXAMPLE 4

Preparation of 1,7-bis(2-methylenepyrrole)-4-(p-nitrobenzyl)diethylenetriamine.

In 150 mL of ethanol was dissolved 2 g of 1,7-bis(pyrrolecarboxylidine)-4-(p-nitrobenzyl)diethylenetriamine (prepared in Example E) and 2 g of sodium borohydride was added. The reaction mixture was stirred at room temperature for 2 hours. The solvent was evaporated and the residue was dissolved in 200 mL of water. The product was extracted in chloroform twice (150 mL portions). Any trace of water was removed from the extract by the addition of about 40 g of anhydrous sodium sulphate. The product was filtered and the chloroform removed by rotary evaporation to provide 1,7-bis(2-methylenepyrrole)-4-(p-nitrobenzyl)diethylenetriamine and was characterized by: $^1$H NMR (CDCl$_3$), carbon protons only; amine and pyrrole protons were not included: δ 2.5 (s, 8H), 3.6 (s, 2H), 3.8 (s, 4H), 6.1 (m, 6H), 7.4–8.1 (m, 4H).

EXAMPLE 5

Preparation of 1,7-bis(2-methylenepyrrole)-4-(p-aminobenzyl)diethylenetriamine.

Reduction of 300 mg of 1,7-bis(2-methylenepyrrole)-4-(p-nitrobenzyl)diethylenetriamine (prepared in Example 4) in 100 mL of ethanol was preformed using 100 mg of palladium on activated charcoal (10% Pd). The mixture was hydrogenated at 48 psi (331 kPa) for 48 hours. The catalyst was removed by filtration. The ethanolic solution was evaporated to provide 1,7-bis(2-methylenepyrrole)-4-(p-aminobenzyl)diethylenetriamine, and was characterized by: $^1$H NMR (CDCl$_3$), carbon protons only; amine and pyrrole protons were not included: Free amine: δ 2.5–2.7 (m, 8H), 3.5 (s, 2H), 3.7 (s, 4H), 6–6.2 (m, 3H), 6.5–6.7 (m, 3H), 6.9–7.2 (m, 4H); HCl salt: δ 6.7–7.0 (2d, 4H), 3.35–3.55 (broad s, 12H), 3.25 (s, 2H), 1.49 (s, 12H).

EXAMPLE 6

Preparation of 2,2,12,12-tetramethyl-4,7,10-triaza-7-(p-aminobenzyl)-1,3-tridecane dithiol.

The crude 2,2,12,12-tetramethyl-4,7,10-triaza7-(p-aminobenzyl)-1,13-tridecadiene-1,13-dithiol (prepared in Example G), 2.75 g (0.00671 mol) was dissolved in 25 mL of dry tetrahydrofuran and added dropwise with cooling, under a nitrogen atmosphere, to a stirred suspension of (0.02 mol) of lithium aluminium hydride. The mixture was heated under reflux for 40 hours and subsequently hydrolyzed by the cautious addition of about 50–75 mL of saturated sodium and potassium tartarate solution. To the mixture was then added 300 mL of diethyl ether. The sludge was separated by decanting or filtration (celite) and washed well with diethyl ether. Subsequently the solution was washed with brine and the organic layer was separated and dried over sodium sulfate. The solvent was cautiously evaporated to dryness. The residue was dissolved in anhydrous diethyl ether and treated with hydrogen chloride gas. The sticky product precipitated as the hydrochloride salt and was characterized by: $^1$H NMR (CDCl$_3$) δ 1.51 (s, 12H), 2.65 (t, 4H), 3.29–3.68 (m, 1OH), 6.6–6.9 (2d, 4H). $^{13}$C NMR (CDCl$_3$) δ 27.43, 48.23, 53.25, 54.13, 58.43, 59.17, 122.67, 128.05, 129.71, 144.5.

PREPARATION OF COMPLEX AND CONJUGATE FINAL PRODUCTS

EXAMPLE 7

Complexation of $^{105}$Rh with bis(2-hydroxybenzyl)-4-(p-aminobenzyl)diethylenetriamine and the conjugation to IgG.

A. Complexation of $^{105}$Rh with bis(2-hydroxybenzyl)-4-(p-aminobenzyl)diethylenetriamine Complexation of bis(2-hydroxybenzyl)-4-(p-aminobenzyl)diethylenetriamine (prepared in Example 2) with rhodium was tried at different concentrations of the ligand as well as carrier rhodium. Typically, 0.5 mL of sodium bicarbonate buffer (0.5M, pH 9, 0.1 mL) and $^{105}$Rh (15 MBq) and 0.05 mL of RhCl$_3$ (1.25×10$^{-3}$ mmol) (i.e. carrier rhodium) were mixed together and refluxed for about 10 min in a 10 mL round bottom flask fitted with a glass condenser over a boiling water bath. To this reaction mixture was added 0.5 mL (1.5×10$^{-3}$ mmol) of an ethanolic solution of the ligand. The mixture was then further refluxed for 2 hours and the mixture turned yellow.

The solution was cooled to room temperature and transferred to a 10 mL centrifuge tube. Upon cooling, the solution turns green. After a 10 μL aliquot (first) was removed, the remaining solution was centrifuged for 15 min. The clear supernatant solution was transferred to another vial. A 10 μL aliquot (second) was removed and counted for radioactivity (in a NaI(Tl) scintillation counter after suitable modification of the geometry). By comparing the activity of the second aliquot with the activity in the first aliquot, the amount of activity lost as sediments was calculated. The final concentration of Rh in solution was calculated by taking into account this loss of activity and the total volume after heating.

Complex yields were estimated by an MgO adsorption technique. This method is based on the observation that inorganic rhodium complexes are adsorbed by MgO leaving behind the organic complexes in solution. Typically, 10 μL of the complex solution was diluted to 0.4 mL and about 50 mg of MgO powder was added and mixed over a vortex mixer for 2 min followed by a 5 min centrifugation. The supernatant was separated and both fractions counted. The activity associated with the supernatant was an estimate of the complex present.

The results of the complexation are shown in Table 1 which shows the complex prepared with different Rh to ligand ratios. The ligand/metal ratio varied from 1 to 5 in the experiments with carrier rhodium. In the experiment where there was no carrier added rhodium, the ligand is present in a concentration at about 10$^6$ higher than rhodium.

The amount of rhodium activity lost as sediments varied from 5–15%. Column 6 in Table 1 shows the yield estimated by MgO adsorption technique. The complex yield in solution after removal of sediments varied between 85–91%. The overall complex yields were calculated by taking into account the activity in solution and complex yield in solution as estimated by MgO adsorption technique. The overall complex yields, calculated by multiplying the activity yield in solution by complex yields, were between 75–83%.

TABLE 1

| RUN | [Rh] $\times 10^{4a}$ | [L] $\times 10^{3a}$ | L/Rh | %$^b$ Activity in solution | %$^c$ Complex in solution | %$^d$ Complex yield | %$^e$ Activity in chloroform | %$^f$ Conjugation | %$^g$ Overall yield | Rh/IgG$^h$ |
|---|---|---|---|---|---|---|---|---|---|---|
| 1 | 12.5 | 1.25 | 1 | 85 | 91 | 78 | 82 | 87 | 61 | 1.7 |
| 2 | 5 | 1.25 | 2.5 | 91 | 90 | 82 | 85 | 92 | 71 | 0.8 |
| 3 | 2.5 | 1.25 | 5 | 88 | 85 | 75 | 79 | 90 | 62 | 0.4 |
| 4 | NCA | 12.5 | NCA | 95 | 87 | 83 | 76 | 92 | 66 | NCA |

L is bis(2-hydroxybenzyl)-4-(p-aminobenzyl)diethylenetriamine
NCA means No Carrier Added
$^a$total volume of reaction 2.1 mL (e.g. Run 1: Rh = 12.5 $\times$ 10$^{-4}$M, L = 1.25 $\times$ 10$^{-3}$M)
$^b$% of total activity in solution
$^c$% of which complexed
$^d$% of total activity converted to complex (e.g. Run 1: 0.85 $\times$ .91 = 0.78)
$^e$% of activity in solution extracted into chloroform after conversion to isothiocyanate
$^f$% of activity extracted into chloroform conjugated to protein
$^g$overall yield = % activity in solution (b) $\times$ % activity in chloroform (e) $\times$ % activity in conjugation (f)
$^h$the average number of Rh atoms per IgG molecule In table 1, conjugation reactions were run such that [L] (based on data) (a)/[IgG] was always 2.8 and the atoms of Rh/molecule IgG=2.8$\times$(g)$\times$(Rh/L from(a)). For example, Run 1: 2.8$\times$0. 61$\times$1=1.7; and Run 2: 2.8$\times$0.71$\times$1/2.5=0.8.

Table 2 gives the complexation yield studied for the reaction carried out at different concentration of bis-(2-hydroxybenzyl)-4-(p-aminobenzyl)diethylenetriamine and rhodium. The rhodium to bis-(2-hydroxybenzyl)-4-(p-aminobenzyl)diethylenetriamine ratio was kept constant at 1 except for the reaction with no carrier added rhodium. The complexation reaction was clean in all these cases with better than 96% of the activity in solution after centrifugation. The complex yield in solution varied between 87-94%. Overall complex yields varied between 85-90%. In Table 2, the conjugation reactions were run such that the ligand (L), based on data) (a)-/IgG was always 1.12. Calculations were the same as for Table 1.

the activity was transferred into the organic layer. As the extractability of the complex itself was not very high, the higher extractability seen after activation was assumed to be due to the higher partition coefficient of the activated complex. The partition coefficient of the isothiocyanate derivative of the complex was estimated by repeated back extractions of it into saline and was found to be around 60.

B. Preparation of the isothiocyanate derivative.

The isothiocyanate derivative of the complex from Part A above was prepared by treating an aqueous solution of the complex with an excess concentration of thiophosgene in chloroform. The isothiocyanate derivative of the complex is referred to as the activated complex.

Typically 1 mL of the complex (about 7$\times$10$^{-4}$ mmol) prepared above was mixed for 2 min with 0.1 mL (1.3$\times$10$-$2 mmol) of thiophosgene, diluted in chloroform, over a vortex mixer. The majority of the activity,

TABLE 2

| RUN | [Rh] $\times 10^{4a}$ | [L] $\times 10^{4a}$ | L/Rh | %$^b$ Activity in solution | %$^c$ Complex in solution | %$^d$ Complex yield | %$^e$ Activity in chloroform | %$^f$ Conjugation | %$^g$ Overall yield | Rh/IgG$^h$ |
|---|---|---|---|---|---|---|---|---|---|---|
| 1 | 12.5 | 12.5 | 1 | 96 | 94 | 90 | 84 | 86 | 70 | 0.8 |
| 2 | 5 | 5 | 1 | 96 | 89 | 85 | 83 | 93 | 75 | 0.8 |
| 3 | 2.5 | 2.5 | 1 | 100 | 87 | 87 | 82 | 90 | 74 | 0.8 |
| 4 | NCA | 2.5 | NCA | 100 | 88 | 87 | 69 | 90 | 62 | NCA |

L is bis(2-hydroxybenzyl)-4-(p-aminobenzyl)diethylenetriamine
NCA means No Carrier Added
$^a$total volume of reaction 2.1 mL (e.g. Run 1: Rh = 12.5 $\times$ 10$^{-4}$M, L = 1.25 $\times$ $^{-3}$M)
$^b$% of total activity in solution
$^c$% of which complexed
$^d$% of total activity converted to complex (e.g. Run 1: 0.96 $\times$
$^e$% of activity in solution extracted into chloroform after conversion to isothiocyanate
$^f$% of activity extracted into chloroform conjugated to protein
$^g$overall yield = % activity in solution (b) $\times$ % activity in chloroform (e) $\times$ % activity in conjugation (f)
$^h$the average number of Rh atoms per IgG molecule In Table 2, the conjugation reactions were in a manner analogous to that of Table 1.

The extractability of the complex in chloroform was estimated. This varied from 20-35% in different batches. A back extraction of the complex from the organic layer into saline gave 67% of the activity still remaining in the organic layer. However, the second extraction of the aqueous layer gave only 9% of the activity in the organic layer. These results suggests the possibility of the presence of more than one species of complex in solution.

Tables 1 and 2 give the activity transfer into the organic layer during the reaction with thiophosgene. Note that only 0.1 mL of chloroform was used for extraction as against 1 mL of complex solution. The majority of which was believed to be due to the activated complex, was transferred into the organic layer. The aqueous layer was carefully withdrawn into another tube. The amount of activity transferred into the organic layer is calculated by counting a 10 $\mu$L aliquot of the aqueous layer before and after activation. The organic layer was dried under a stream of nitrogen gas to remove any chloroform and unreacted thiophosgene. The dried activated complex was dissolved into 100 $\mu$L dimethylformamide and used for conjugation.

C. Conjugation.

IgG, 2 mL, dissolved in 0.1M borate buffer, pH 9 containing 0.15M NaCl, was mixed with 20 $\mu$L (10$^{-4}$ mmol) of the activated complex in dimethylformamide.

The conjugation reaction was carried out at room temperature for 4–5 hours.

D. Estimation of conjugation yields.

The conjugation yields were estimated by gel permeation chromatography. A 30×1.4 cm column was packed with presoaked Sephedex ™ G 75 gel and equilibrated by passing 100 mL of 0.15M NaCl solution through the column. The reaction mixture, 0.1 mL, was applied to the top of the column and eluted with 0.15M NaCl solution. Fractions of 2 mL each were collected and the activity measured in a NaI(T1) scintillation counter. Recovery from the column was monitored by counting an equal aliquot, after dilution to 2 mL, and comparing it with the sum of the activity eluted from the column. Activity associated with the protein peak was summed and compared to the total activity for the estimate of the yield of conjugation.

Conjugation studies, with complex prepared at different bis-(2-hydroxybenzyl)-4-(p-aminobenzyl)diethylenetriamine to Rh ratios and also at different concentrations of Rh, gave high conjugation yields (Tables 1 and 2 before). Yields varied from 86–93% and was found to be independent of the complexation condition. In conjugation experiments with different bis-(2-hydroxybenzyl)-4-(p-aminobenzyl)diethylenetriamine/Rh ratios, the reaction was performed with the ligand:IgG ratio at 2.8:1. Note that the ligand concentrations used are based on the data (a). The actual amount of ligand still present at the time of conjugation is not known. The equations given for Table 1 convert the ratio to the Rh/IgG actually conjugated. In these studies since excess ligand was used for complexation all the ligand was not utilized for complexation and hence there is free ligand present. The number of rhodium atoms incorporated in these studies varied from 0.4–1.7 depending upon the starting Rh ratio. The overall rhodium recovery at the end of the conjugation reaction varied from 61 to 71% without taking into account the activity loss due to decay.

In the conjugation experiments with Rh/bis-(2-hydroxybenzyl)-4-(p-aminobenzyl)diethylenetriamine ratio kept constant at 1 (Table 2), the number of Rh atoms incorporated was from 0.8–1.12. Note that the ligand/IgG ratio was kept constant at 1.12 in these conjugation experiments. The final rhodium recovery in these experiments varied from 70–75%.

Table 3 gives the results of conjugation studies with different Rh to IgG ratios while keeping the IgG concentration constant and varying the complex concentration. The complex used in this study was prepared at 1:1Rh/Ligand and the complex yield was 95%. The conjugation yield varied from 85–93% and we could incorporate 0.5–8.5 mmols of Rh per mmol of antibody. The overall Rh yield in these studies varied from 69–75% taking into account activity lost in all steps.

TABLE 3

| [IgG] × $10^5$ | [Rh] × $10^5$ | Rh/IgG | Conjugation % | Rh/IgG[a] Labeled | % Rhodium[b] Yield |
|---|---|---|---|---|---|
| 5 | 2.5 | 0.5 | 91 | 0.5 | 74 |
| 5 | 5 | 1 | 93 | 0.9 | 75 |
| 5 | 10 | 2 | 93 | 1.9 | 75 |
| 5 | 25 | 5 | 92 | 4.6 | 74 |
| 5 | 50 | 10 | 85 | 8.5 | 69 |

[a]This is the number of rhodium atoms incorporated per molecule of IgG
[b]Calculated by taking into account activity lost as sediments, lost aqueous layer and the conjugation yield.

Table 4 gives the results of conjugation yield studied with different ratios of protein and complex. The concentration of complex is kept constant and the concentration of IgG varied with Rh/IgG from 1–10. It was seen that the yield decreased from 91–73% when IgG concentration was reduced from $5 \times 10^{-5}$ to $5 \times 10^{-6}$ mmol. The number of Rh/atoms incorporated per IgG molecule varied from 0.9–7.3 in these experiments. These results suggest that there is greater dependence on the concentration of IgG than that of the activated complex for conjugation.

TABLE 4

| [IgG] × $10^6$ | [Rh] × $10^5$ | Rh/IgG | Conjugation % | Rh/IgG[a] Labeled | % Rhodium[b] Yield |
|---|---|---|---|---|---|
| 50 | 5 | 1 | 91 | 0.9 | 74 |
| 20 | 5 | 2.5 | 87 | 1.8 | 70 |
| 10 | 5 | 5 | 84 | 14.2 | 68 |
| 50 | 5 | 10 | 73 | 7.3 | 69 |

[a]This is the number of rhodium atoms incorporated per molecule of IgG
[b]Calculated by taking into account activity lost as sediments, lost aqueous layer and the conjugation yield.

E. EDTA challenge.

The purified protein, 2 mL, equivalent to $4.5 \times 10^{-5}$ mmol of the complex, was mixed with 20 μL of 0.1M EDTA solution and then incubated for 24 hours. The activity associated with the protein and EDTA fractions was estimated by gel permeation chromatography.

The results of the EDTA challenge studies show that Rh complex is highly inert and cannot be exchanged with other ligands at room temperature even at very high concentration of competing ligands. After a 24 hours challenge study, 92% of the activity was still seen with the protein peak on chromatography. No separate peak was seen for EDTA or free complex when labeled protein solution challenged with EDTA was rechromatographed.

F. Affinity chromatography.

Affinity chromatography was done on an anti-IgG agarose gel column. Two mL of the gel was packed into a syringe column and equilibrated with 20 mL of 0.01M phosphate buffer, pH 7.2. The solution from the conjugate reaction mixture, 50 μL, was applied to the top of the column. Non-immunoreactive fractions were collected in 10 mL of phosphate buffer. Antibody bound IgG was eluted with 0.05M acetic acid containing 0.2M sodium acetate, pH 2.5. Fractions, 1 mL, were collected and activity monitored on a NaI (T1) gamma scintillation counter.

Affinity chromatography of the labeled IgG from Run 3, Table 2 gave 81% of the activity retention in the affinity column as against 90% yield of conjugation. This indicates that 90% of the labeled IgG retained immunoreactivity after conjugation. Labeled proteins from all the runs were not studied by affinity chromatography, instead an affinity adsorption study was done which is less time consuming and has the advantage that multiple samples can be handled. However, the actual percentage of immunoreactive component present is not given but only an index. The results of affinity adsorption studies are shown in Table 5. Labeled IgG prepared in different batches showed greater than 61% adsorption to the affinity gel. The unactivated complex of bis-(2-hydroxybenzyl)-4-(p-aminobenzyl)diethylenetriamine was run with the affinity gel under similar conditions and found that less than 5% of the activity was retained in the affinity gel after the third wash.

TABLE 5

| Table | Run | Adsorption on affinity gel |
|---|---|---|
| 1 | 1 | 60 |
| 1 | 2 | 63 |
| 1 | 3 | 66 |
| 1 | 4 | 60 |
| 2 | 1 | 60 |
| 2 | 2 | 74 |
| 2 | 3 | 77 |
| 2 | 4 | 71 |

G. Affinity adsorbtion studies.

Affinity gel, 1 mL, was incubated with 25 μL (about 0.2 mg of IgG) of the solution from the conjugation reaction for 15 min with gentle shaking. The gel was washed (3 times, 2 mL) with phosphate buffer to remove unbound activity. After the third wash the gel was counted for radioactivity. The original solution, 25 μL was also counted for radioactivity under identical conditions. The percentage retention of activity to the gel was calculated by comparing the activity in the gel with total activity.

H. Conjugation kinetics.

Time dependence of the conjugation reaction was studied by incubating 80 μL of the activated complex ($1.5 \times 10^{-4}$ mmol) with 3 mL of IgG solution ($5 \times 10^{-5}$ M). This solution, 100 μL, was withdrawn at various time intervals and conjugation yield estimated by gel permeation chromatography.

I. Stability of activated complex.

The chloroform extract of the activated complex, 40 μL, (about $10^{-4}$ mmol) was dispensed into tubes and dried under nitrogen. The tubes were sealed and stored at room temperature. One tube was taken at different time intervals and the contents dissolved in 50 μL of dimethylformamide. Then a 25 μL aliquot of the solution was added to 1 mL of IgG solution ($5 \times 10^{-5}$ mmol). The conjugation reaction was carried out for 5 hours and the yield estimated by gel permeation chromatography.

Table 6 gives the results of conjugation studies carried out with activated complex stored for different time intervals. No significant difference was seen with activated complex stored up to 4 days on conjugation.

TABLE 6

| Time (hours) | Conjugation % |
|---|---|
| 0 | 90 |
| 24 | 89 |
| 48 | 90 |
| 72 | 94 |
| 96 | 92 |

EXAMPLE 8

Complexation of $^{99m}$Tc with bis(2-hydroxybenzyl)-4-(p-aminobenzyl)diethylenetriamine and the conjugation to IgG.

A. Complexation of $^{99m}$Tc with bis(2-hydroxybenzyl)-4-(p-aminobenzyl)diethylenetriamine.

The complex of $^{99m}$Tc with bis(2-hydroxybenzyl)-4-(p-aminobenzyl)diethylenetriamine (prepared in Example 2) was prepared using saturated tin tartarate solution as the reducing agent. Before adding the tin tartarate solution to the complexation mixture, it was purged with nitrogen and centrifuged to remove solid particles. The complexation mixture was then prepared from 0.5 mL of bicarbonate buffer (0.5M, pH 9), 0.2 mL of bis(2-hydroxybenzyl)-4-(p-aminobenzyl)-diethylenetriamine ($5 \times 10^{-4}$ mmol) in ethanol, 1 mL $^{99m}$Tc (37–74 MBq) and 2.6 mL of 0.9% saline solution. The complexation mixture was mixed over a magnetic stirrer. To this mixture was added 0.2 mL of the tin tartarate solution and the mixture was mixed over a magnetic stirrer for 10 min.

B. Paper Chromatography and thin layer chromatography.

To two 1×13.7 cm solvent saturation pads (Gelman Sciences Inc.) was applied 5 μL of the complex solution (prepared in Example 7A). The pads were developed in acetone and 0.9% saline. After drying the solvents, the papers were cut into 6 sections and counted for radioactivity. The whole chromatograph was divided into 2 parts—from the point of spotting to the middle of the paper and from the middle of the paper to the solvent front—and the percentage of activity associated with these two fractions computed.

Thin layer chromatography was carried out on 2.5×7.5 cm flexible silica gel plates. The solution (5 μL) was spotted about 1 cm from the end of the plate and then developed in saline up to 7 cm. The plates were removed, dried and cut into 10 strips of equal size. The strips were counted for radioactivity in a well-type NaI (T1) counter. Percentages of the complex activity at the point of spotting and solvent front were calculated.

The distributions of complex activity in paper and thin layer chromatography is given in Table 7. In using paper chromatography, with both acetone and saline as eluents, 75–80% of the activity was seen at the solvent front. In thin layer chromatography using saline as eluent, 19% of the activity was seen at the solvent front. In control experiments, $TcO_4^-$ was seen at solvent front in thin layer chromatography/saline.

TABLE 7

| Method | Distribution of Activity | |
|---|---|---|
| | Rf = 0 | Rf = 1 |
| PC/SALINE | 21 | 79 |
| PC/ACETONE | 24 | 76 |
| TLC/SALINE | 81 | 19 |

In Table 2, PC means paper chromatography, and TLC means thin layer chromatography.

C. HPLC (High Performance Liquid Chromatography)

HPLC analyses were done in Beckman model 332 gradient liquid chromatographic system. Eluent radioactivity was measured by Beckman TM model 170 radioisotope detector. A Hamilton TM PRP-1 reverse phase column (30.5 cm) was used for complex analysis. Samples of 15 μL were injected into the column. A gradient elution using water (A) and acetonitrile (B) was used with a flow rate of 2 mL/min. Typically the flow pattern was:

concentration of B in A
0–2 min 10% B
2–4 min linear gradient of 70% B
4–18 min 70% B
38–40 min 10% B linear gradient After completion of each run, the column was equilibrated for 10 min with 90% A and 10% B solution. Between each run the injection port was flushed with methanol. When the column was not in use it was kept in 9/1 B/A. $TcO_4^-$ was eluted at $R_t = 1.0$ min. and the complex at $R_t = 7.0$–7.5 min. Complex was eluted mainly as a single peak. $TcO_4^-$ estimated by this method was about 20%.

D. Solvent Extraction

The lipophilic complex formed was extracted into chloroform. The reaction mixture, 4 mL, was mixed with 4 mL of chloroform and further mixed with a vortex mixer for 2 min. The organic and aqueous layers were separated. A second extraction was carried out by mixing 1 mL of the aqueous layer with 1 mL of chloroform and extracted as before. One mL of the organic layer from the first extraction was back extracted with 1 mL of 0.1M NaHCO$_3$ buffer, pH 9.0. The partition coefficient was calculated from the back extraction data.

The complex showed very high extractability in chloroform. The extraction yield in different batches varied from 85–95%. The second extraction yield was generally low, 10% of the remaining activity. The chloroform/buffer partition coefficient was about 90. This high partition coefficient enables quantitative separation of the complex by a single extraction.

The complexation reaction is complete in 5–10 min. About 95% of the activity could be extracted into chloroform for the first one hour of complexation. Prolonged reaction resulted in less extractable activity. After a 24 hour reaction the solvent extractable activity was only 55%.

E. Preparation of the isothiocyanate derivative.

To 3 mL of the organic layer ($3 \times 10^{-4}$ mmol of the ligand) was added 0.5 mL of thiophosgene ($3.3 \times 10^{-2}$) diluted in chloroform and the the mixture stirred for 2 min. Excess thiophosgene and chloroform were removed by evaporation under a flow of nitrogen. The activated complex was then dissolved into 0.6 mL of dimethylformamide to give a ligand concentration of $5 \times 10^{-4}$ mmol/mL.

F. Conjugation to protein.

Conjugation of the activated complex from part E above to protein (IgG) was carried out in 0.1M borate buffer, pH 9.0 containing 0.9% saline. To 1 mL IgG ($5 \times 10^{-5}$ mmol) was added activated complex solution, varying from $5 \times 10^{-6}$ to $10^{-4}$ mmol, and the solution was incubated for 2–4 hours. The ligand/IgG ratio varied from 0.1 to 2.0. Note that those ratios are based on the amount of ligand used to form the complex. Since the concentration of $^{99m}$Tc is so much lower than the ligand, the ligand concentrations are shown only to demonstrate the affects of amounts of complex on the conjugation.

In an alternate experiment, ligand concentration was maintained constant at $5 \times 10^{-5}$ mmol/mL. IgG concentration was varied from $5 \times 10^{-5}$ to $10^{-4}$ mmol/mL. The reaction volume in this instance was 0.25 mL. A blank experiment was carried out by incubating 0.5 mL of the unactivated complex ($5 \times 10^{-5}$ mmol) with 1 mL of IgG solution ($5 \times 10^{-5}$ mmol) for 4 hours.

G. Estimation of conjugation yields.

Conjugation yields were estimated by gel permeation chromatography over Sephadex TM G 75 column (30×1.4 cm). An aliquot of the reaction mixture was applied on the top of the column and eluted with 0.9% saline solution. Fractions, 2 mL, were collected and the activity measured in a NaI (Tl) scintillation counter. An equal amount of the sample applied to the column was diluted to 2 mL and kept as a control. Recovery from the column was calculated by comparing the sum of activity eluted from the column to the activity in the control tube. The conjugation yield was calculated by taking the ratio of the sum of the protein peak to the total recovered activity.

Table 8 shows the conjugation yields when IgG concentration is kept constant and the ligand concentration varied to give different complex/IgG ratios. The conjugation yield was 67% at a ratio of 0.1 complex/IgG but remained constant around 79% from 0.5 to 2.0. The low yield seen at the ratio of 0.1 complex/IgG may be due to the slower kinetics of these reactions at this concentration.

TABLE 8

| [IgG] × 10$^5$ | [Complex] × 10$^6$ | Complex/IgG | % Yield |
|---|---|---|---|
| 5 | 5 | 0.1 | 67 |
| 5 | 25 | 0.5 | 79 |
| 5 | 50 | 1.0 | 80 |
| 5 | 100 | 2.0 | 79 |

Table 9 gives conjugation yield when complex concentration is kept constant and IgG concentration varied from 1 to 5. At the lowest concentration of protein ($10^{-5}$), the yield was >70%. The amount of protein used at this level was 375 μg.

TABLE 9

| [IgG] × 10$^5$ | [Complex] × 10$^5$ | Complex/IgG | % Yield |
|---|---|---|---|
| 5 | 5 | 1 | 73 |
| 2.5 | 5 | 2 | 74 |
| 1.0 | 5 | 5 | 71 |

When unactivated complex was incubated with IgG and chromatographed in a Sephadex TM column, only 3% of the activity was seen with the protein. The rest of the activity was eluted between 30 and 50 mL.

H. EDTA challenge.

A 2 mL fraction of the protein peak, isolated from the gel permeation chromatography, was incubated with 10 μL of $10^{-1}$M EDTA solution and incubated for 24 hours. The EDTA/ligand ratio was 200 and 400 in the two sets of experiments. Activity associated with EDTA and protein was estimated by gel permeation chromatography as described before.

Results of the EDTA challenge studies are given in Table 10. Recovery from the gel permeation column was 84%. More than 95% of the recovered activity was seen with IgG.

TABLE 10

| EDTA/ Complex | % Recovery from the column | % Activity with IgG | % Activity with EDTA |
|---|---|---|---|
| 200 | 84 | 82 | 2 |
| 400 | 84 | 80 | 4 |

EXAMPLE 9

Complexation of $^{57}$Co with bis(2-hydroxybenzyl)-4-(p-aminobenzyl)diethylenetriamine and the conjugation to IgG.

A. Complexation of $^{57}$Co with bis(2-hydroxybenzyl)-4-(p-aminobenzyl)diethylenetriamine.

A $10^{-2}$ mmol solution of Co(II) was prepared by dissolving Co(II) perchlorate in saline. 0.1 mL of this solution was spiked 2 μL of $^{57}$Co (about 20 μCi) and equilibrated for 24 hours.

Complexation was carried out by mixing 100 μL ($2.5 \times 10^{-4}$ mmol) of bis(2-hydroxybenzyl)-4-(p-aminobenzyl)diethylenetriamine (prepared in Example 2), with 10 μL of Co(II) solution ($10^{-4}$ mmol) and incubating for hour. Complex yield was estimated by thin layer chromatography using saline as eluent. Complex has an $R_f=0$ free Co(II) has an $R_f=1.0$. The results of the complexation reaction are shown in Table 11.

TABLE 11

| Ligand (mmol) | Co(II) (mmol) | Ligand/Co(II) | % Complex |
|---|---|---|---|
| $10^{-4}$ | $10^{-4}$ | 1 | 18 |
| $2.5 \times 10^{-4}$ | $10^{-4}$ | 2.5 | 97 |
| $5 \times 10^{-4}$ | $10^{-4}$ | 5 | 97 |

Complexation yield was highly dependent on the ligand to Co(II) ratio. At ligand to Co(II) ratio greater than 2.5, complexation yield was greater than 97%.

B. Activation.

To the complex was added 5 μL ($6 \times 10^{-2}$ mmol) of $CSCl_2$ and then the solution was mixed for 2 min over a vortex mixer. The activated complex was dried and the solid dissolved in 100 μL of dimethylformamide.

C. Conjugation.

The activated complex ($2.5 \times 10^{-5} - 1.25 \times 10^{-4}$ mmol) in dimethylformamide was mixed with IgG ($5 \times 10^{-5}$ mmol) in borate solution and incubated for 24 hours at room temperature. Conjugation yields were estimated by gel permeation chromatography using a Sephedex ™ G 75 column ($30 \times 1.4$ cm). Saline solution (0.9%) was used as eluent. The results of the conjugation reaction are given in Table 12.

TABLE 12

| IgG (mmol) | Activated complex (mmol) | Complex/IgG | % Yield |
|---|---|---|---|
| $5 \times 10^{-5}$ | $2.5 \times 10^{-5}$ | 0.5 | 52 |
| $5 \times 10^{-5}$ | $5 \times 10^{-5}$ | 1 | 62 |
| $5 \times 10^{-5}$ | $1.3 \times 10^{-4}$ | 2.5 | 88 |
| $5 \times 10^{-5}$ | $5 \times 10^{-5a}$ | 1 | 40 |
| $5 \times 10^{-5}$ | $5 \times 10^{-5b}$ | 1 | 19 |

$^a$Unactivated complex used to estimate non specific labeling
$^b$Co(II) solution used for estimating non specific labeling due to free cobalt.

D. Non-specific labeling.

Non-specific labeling was estimated by using unactivated complex and Co(II) solution spiked with $^{57}$Co. In the former case, the complex was dried and dissolved in 100 μL of dimethylformamide and 20 μL ($5 \times 10^{-5}$ mmol) of this solution was incubated with 1 mL of IgG ($5 \times 10^{-5}$ mmol) for 24 hours. In the latter case, 5 μL ($5 \times 10^{-5}$ mmol) of Co(II) solution spiked with $^{57}$Co was incubated for 24 hours with 1 mL of IgG ($5 \times 10^{-5}$ mmol). Non-specific labeling yields in both cases were estimated by gel permeation chromatography. The non-specific labeling yields were high for unactivated complex. See Table 12 above.

EXAMPLE 10

Complexation of $^{105}$Rh with 1,7-bis(2-methylenepyrrole)-4-(p-aminobenzyl)diethylenetriamine and the conjugation to IgG.

A. Complexation of $^{105}$Rh with 1,7-bis(2-methylenepyrrole)-4-(p-aminobenzyl)diethylenetriamine.

One mL of $1 \times 10^{-3}$M solution of $RhCl_3$ was spiked with 50 μL of $^{105}$Rh (about 120 μCi) and then warmed to attain equilibrium between the carrier and active rhodium. To the solution was added $1.25 \times 10^{-3}$ mmol (1 mL) of 1,7-bis(2-methylene-pyrrole)-4-(p-aminobenzyl)diethylenetriamine (prepared in Example 5). This mixture was refluxed for 2 hrs. Complexation yield was estimated by the MgO method (as described in Example 7).

The complexation yield was independent of the $^{105}$Rh/ligand ratio as it was always in the range of 77-80% even when carrier free $^{105}$Rh was used.

B. Kinetics of the Complexation Reaction.

To determine the refluxing time needed for complete complexation, the yield was estimated at different refluxing times, 1-180 min, by the MgO method (as described in Example 6). The results of the kinetics experiments are given in Table 13. The complex yield was found to reach its maximum after only 5 minutes of refluxing.

TABLE 13

| Time (Min) | Yield % |
|---|---|
| 1 | 72 |
| 5 | 79 |
| 10 | 79 |
| 30 | 79 |
| 60 | 78 |
| 180 | 75 |

The percent of the total activity extracted into the organic phase was about 62%. The yield values in Table 11 above are based on the organic phase only.

C. Activation.

To 1 ml of the complex (prepared in Part B above) was added $1.3 \times 10^{-2}$ mmol $CSCl_2$ in 1 mL of chloroform. The solution was mixed for 2-3 min. The organic layer was separated and dried and the residue dissolved in 150 μL of DMF.

D. Conjugation to protein.

The activated complex, 50 μl, (prepared in Part C) was added to 2 mL of IgG ($1 \times 10^{-4}$ mmol) in borate buffer and then incubated for 24 hours at room temperature. The conjugation yield was estimated by gel permeation chromatography.

Conjugation yield with IgG ranged from 88-97%. The ratio of complex to protein was not determined because the coupling work was performed with carrier free $^{105}$Rh. Overall yields then are (about $0.62 \times 0.92$) or about 57%.

E. Blank

Unactivated complex was incubated with IgG for 24 hours at room temperature. The yield was estimated by gel permeation chromatography. The non-specific binding of the unactivated complex was 25-27%.

EXAMPLE 11

Complexation of $^{99m}$Tc with 2,2,12,12-tetramethyl-4,7,10-triaza-7-(p-aminobenzyl)-1,13-tridecane dithiol.

A. Complexation of $^{99m}$Tc with 2,2,12,12-tetramethyl-4,7,10-triaza-7-(p-aminobenzyl)-1,13-tridecane dithiol.

The complex of $^{99m}$Tc with 2,2,12,12-tetramethyl-4,7,10-triaza-7-(p-aminobenzyl)-1,13-tridecane dithiol (prepared in Example 6) was prepared by the stannous tartrate reduction method. The complexation mixture was prepared from 0.5 mL of bicarbonate buffer (0.5 mol, pH 9), 0.1 mL of 2,2,12,12-tetramethyl-4,7,10-triaza-7-(p-aminobenzyl)-1,13-tridecane dithiol ($5 \times 10^{-3}$M) in saline, 1 mL of $^{99m}$Tc (as sodium pertechnetate), 2.2 mL of 0.9% saline solution, and 1 mL of $NH_4TcO_4$ ($1 \times 10^{-7}$M). To this mixture was added 0.2 mL of the saturated tin tartrate solution and the mixture was allowed to stand for 15 min.

B. Paper Chromatography and Thin Layer Chromatrography

On two 1×13.7 cm solvent saturation pads (Gelman Sciences, Inc.) were spotted 10 μL of the complex from Part A above. The pads were developed in acetone and 0.9% saline. After drying the solvents, the papers were cut into 7 sections and counted for radioactivity. The whole chromatograph was divided into 2 parts, namely, from the point of spotting to the middle of the paper and from the middle of the paper to the solvent front. The percent of activity associated with these 2 fronts were computed.

Thin layer chromatrography was carried out on 2.5×7.5 cm flexible silica gel plates. The complex solution, 5 μL, was spotted about 1 cm from the end of the plate and then developed in saline up to 7 cm. The plates were removed, dried and cut out into 10 strips of equal size. The strips were counted for radioactivity in a well type NaI (T1) counter. Percentages of the complex activity at the point of activity and the solvent front were calculated.

In using paper chromatrography with acetone as the eluent, 80% of the activity was seen at the solvent front. In thin layer chromatography using saline as the eluent, no activity was seen at the solvent front indicating nearly 100% complexation, because in control experiments, $TcO_4^-$ was seen at the solvent front in thin layer chromatography with saline as the eluent.

C. High Performance Liquid Chromatograpgy (HPLC)

a. Equipment

HPLC analysis was done using a Beckman model 332 liquid chromatographic system. Eluent radioactivity was measured by a Beckman model 170 radioisotope detector. A Hamilton PRP-1 reverse phase column was used for complex analysis.

b. Process

Samples from Part B above, 20 μL, were injected into the column. A solvent system of methanol and water (80/20 v/v) was used as the eluting solvents with a flow rate of 2 mL/min. $TcO_4^-$ was eluted at $R_t = 1.98$ min. The complex was eluted at $R_t = 5.97$ min. and was a single peak, indicating the presence of a single species. $TcO_4^-$ estimated by this method was about 9%.

D. Solvent Extraction

The reaction mixture from Part C above, 1 mL, was mixed with 1 mL of chloroform and vortexed for 2 min. The organic and aqueous layers were separated and counted. A second extraction was carried out by mixing 1 mL of the aqueous layer with 1 mL of chloroform and extracted as before. The organic layer from the first extraction, 1 mL, was back extracted with 1 mL of $NaHCO_3$ buffer, pH 9.0. The partition coefficient was calculated from the back extraction data.

The complex was highly extractable in chloroform, with a yield in the range of from 80-90%, in studies performed in different batches. The second extraction typically recovered only 8-10% of the remaining activity. The partition coefficient in chloroform/buffer was about 90. This result facilitated a qunatative extraction of the complex by a single extraction.

The complexation reaction was complete in 5-10 min. About 85% of the activity could be extracted into chloroform in that time period. After 24 hours the solvent extractable activity was about 78% for a single extraction.

E. Preparation of the isothiocyanate derivative

To 0.5 mL ($5 \times 10^{-5}$ mmol) of the organic layer from Part D above was added 20 μL ($1.31 \times 10^{-4}$ mmol) of thiophosgene and the reaction mixture stirred for two min. Excess thiophosgene and chloroform were ex-aporated under a stream of nitrogen. The activated complex was then dissolved in 100 μL of dimethylformamide to give $5 \times 10^{-5}$ mmol of the activated complex.

F. Conjugation to Protein

Conjugation of the activated complex from Part E above to protein (IgG) was carried out in 0.1M borate buffer, pH 9.0 containing 0.9% saline. The activated complex was added to 1 mL of IgG ($5 \times 10^{-5}$ mmol) and the solution incubated for 1 hour. Conjugation was thereby done at a complex to protein ratio of 1:1. A blank experiment was carried out by incubating 0.5 mL of the unactivated complex from Part D above ($5 \times 10^{-5}$ mmol) with 1 mL of IgG solution ($5 \times 10^{-5}$ mol) for 2 hours.

G. Estimation of Conjugation Yirelds

Conjugation yields were estimated by gel permeation chromatography over Sephadex ™ G 75 column (30×1.4 cm). An aliquot of the reaction mixture was loaded on the top of the column and eluted with 0.9% saline solution. Two mL fractions were collected and the activity measured in a NaI (T1) scintillation counter. An equal amount of the sample loaded on the column was diluted to 2 mL and kept as a control. Recovery from the column was calculated by comparing the sum of the activity eluted from the column to the activity in the control tube. The conjugation yield was calculated by taking the ratio of the sum of the protein peak to the total recovered activity. The conjugation yield was about 80% at a 1:1 ratio of complex to IgG.

When the unactivated complex was incubated with IgG and chromatographed in a Sephadex ™ column, only 4% of the activity was eluted between 30 and 50 mL, indicating no conjugation of the unactivated complex with the protein.

The fraction with the maximum activity of the conjugated protein was subsequently rechromatographed after 18 hours. Ninety percent of the activity eluted with the protein on passing through a Sephadex ™ G 75 column, indicating that the conjugate was stable for that period of time.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

What is claimed is:

1. A compound which is 2,2,12,12-tetramethyl-4,7,10-triaza-7-(p-aminobenzyl)-1,13-tridecane dithiol.

2. A complex which comprises a compound of the formula

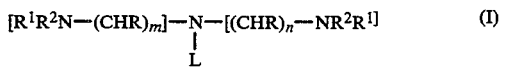

wherein:

R represents independently hydrogen, $C_1$-$C_3$ alkyl, or benzyl;

$R^1$ represents —$CH_2C(CH_3)_2SH$, —$(CH_2)_2NH_2$, —$(CH_2)_2SH$,

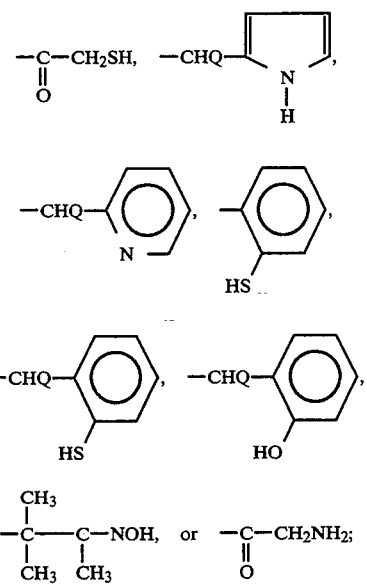

Q represents hydrogen, $C_1$-$C_3$ alkyl or phenyl;

$R^2$ represents hydrogen, —$CH_2CO_2H$, —$CH_2CH_2CO_2H$, or —$(CH_2)_2NH_2$;

m and n are independently 2, 3, or 4;

L is a linker/spacer group covalently bonded to, and replaces one hydrogen atom of the nitrogen atom to which it is joined, said linker/spacer group being represented by the formula

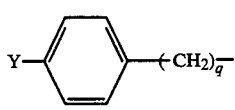 (A)

wherein:

Y is selected from the group consisting of nitro, amino, isothiocyanato, semicarbazido, thiosemicarbazido, carboxyl, bromoacetamido and maleimido;

q is 1, 2, or 3; or a pharmaceutically acceptable salt thereof; and complexed with an ion of a metal selected from the group consisting of $^{99m}Tc$, $^{105}Rh$, $^{109}Pd$, $^{57}Co$, $^{186}Re$, $^{188}Re$, $^{97}Ru$, $^{111}In$, $^{113m}In$, $^{67}Ga$, and $^{68}Ga$.

3. A complex of claim 2 wherein:

m and n are 2 or 3;

$R^2$ is hydrogen;

$R^1$ is

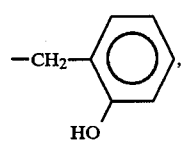

or

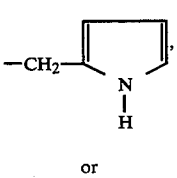

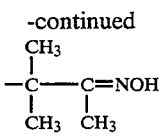

Y is amino or isothiocyanato; or a pharmaceutically acceptable salt thereof.

4. A complex of claim 2 which is $^{105}Rh$ with bis(2-hydroxybenzyl)-4-(p-aminobenzyl)diethylenetriamine.

5. A complex of claim 2 which is $^{99m}Tc$ with bis(2-hydroxybenzyl)-4-(p-aminobenzyl)diethylenetriamine.

6. A complex of claim 2 which is $^{57}Co$ with bis(2-hydroxybenzyl)-4-(p-aminobenzyl)diethylenetriamine.

7. A complex of claim 2 which is $^{105}Rh$ with 1,7-bis(2-methylenepyrrole)-4-(p-aminobenzyl)diethylenetriamine.

8. A complex of claim 2 which is $^{99m}Tc$ with 2,2,12,12-tetramethyl-4,7,10-triaza-7-(p-aminobenzyl)-1,13-tridecane dithiol.

9. A conjugate comprising a compound of the formula

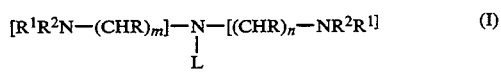 (I)

wherein:

R represents independently hydrogen, $C_1$-$C_3$ alkyl, or benzyl;

$R^1$ represents —$CH_2C(CH_3)_2SH$, —$(CH_2)_2NH_2$, —$(CH_2)_2SH$,

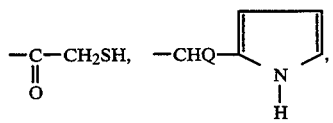

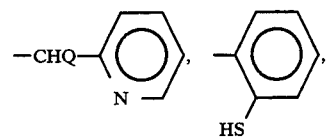

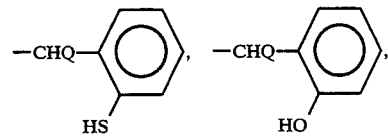

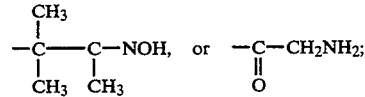

Q represents hydrogen, $C_1$-$C_3$ alkyl or phenyl;

$R^2$ represents hydrogen, —$CH_2CO_2H$, —$CH_2CH_2CO_2H$, or —$(CH_2)_2NH_2$;

m and n are independently 2, 3, or 4;

L is a linker/spacer group covalently bonded to, and replaces one hydrogen atom of the nitrogen atom to which it is joined, said linker/spacer group being represented by the formula

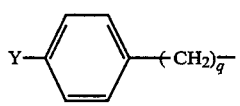

(A)

wherein:
Y is selected from the group consisting of nitro, amino, isothiocyanato, semicarbazido, thiosemicarbazido, carboxyl, bromoacetamido and maleimido;
q is 1, 2, or 3; or
a pharmaceutically acceptable salt thereof;
complexed with an ion of a metal selected from the group consisting of $^{99m}$Tc, $^{105}$Rh, $^{109}$Pd, $^{57}$Co, $^{186}$Re, $^{188}$Re, $^{97}$Ru, $^{111}$In, $^{113m}$In, $^{67}$Ga, and $^{68}$Ga, with the proviso that when $R^2$ is —CH$_2$CO$_2$H or —CH$_2$CH$_2$CO$_2$H, then the radioactive metal ion is selected from the group consisting of $^{186}$Re, $^{188}$Re, $^{99m}$Tc, $^{111}$In, $^{113m}$In, $^{67}$Ga, and $^{68}$Ga; and
covalently attached to a protein or an antibody or antibody fragment.

10. A conjugate of claim 9 wherein:
m and n are 2 or 3;
$R^2$ is hydrogen;
$R^1$ is

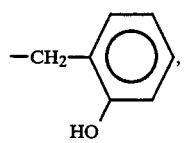

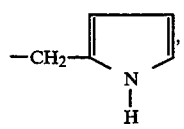

or

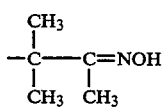

Y is amino or isothiocyanato, or
a pharmaceutically acceptable salt thereof.

11. A conjugate of claim 9 which is the complex of $^{105}$Rh with bis(2-hydroxybenzyl)-4-(p-aminobenzyl)diethylenetriamine to IgG.

12. A conjugate of claim 9 which is the complex of $^{99m}$Tc with bis(2-hydroxybenzyl)-4-(p-aminobenzyl)-diethylenetriamine to IgG.

13. A conjugate of claim 9 which is the complex of $^{57}$Co with bis(2-hydroxybenzyl)-4-(-p-aminobenzyl)diethylenetriamine to IgG.

14. A conjugate of claim 9 which is the complex of $^{105}$Rh with 1,7-bis(2-methylenepyrrole)-4-(p-aminobenzyl)diethylenetriamine to IgG.

15. A conjugate of claim 9 which is the complex of $^{99m}$Tc with 2,2,12,12-tetramethyl-4,7,10-triaza-7-(p-aminobenzyl)-1,13-tridecane dithiol to IgG.

16. A pharmaceutical formulation comprising a conjugate having a compound of the formula

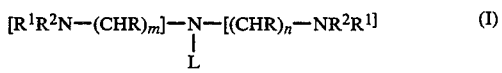

wherein:
R represents independently hydrogen, $C_1$–$C_3$ alkyl, or benzyl;
$R^1$ represents —CH$_2$C(CH$_3$)$_2$SH, —(CH$_2$)$_2$NH$_2$, —(CH$_2$)$_2$SH,

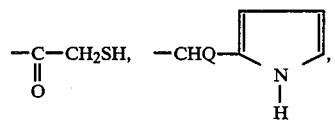

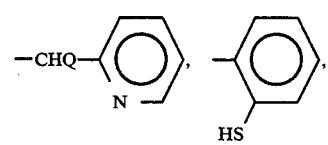

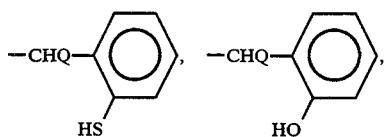

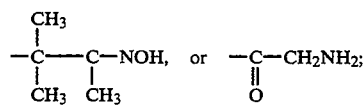

Q represents hydrogen, $C_1$–$C_3$ alkyl or phenyl;
$R^2$ represents hydrogen, —CH$_2$CO$_2$H, —CH$_2$CH$_2$CO$_2$H, or —(CH$_2$)$_2$NH$_2$;
m and n are independently 2, 3, or 4;
L is a linker/spacer group covalently bonded to, and replaces one hydrogen atom of the nitrogen atom to which it is joined, said linker/spacer group being represented by the formula

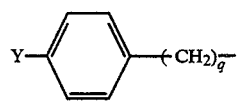

(A)

wherein:
Y is selected from the group consisting of nitro, amino, isothiocyanato, semicarbazido, thiosemicarbazido, carboxyl, bromoacetamido and maleimido;
q is 1, 2, or 3; or
a pharmaceutically acceptable salt thereof; and
complexed with an ion of a metal selected from the group consisting of $^{99m}$Tc, $^{105}$Rh, $^{109}$Pd, $^{57}$Co, $^{186}$Re, $^{188}$Re, $^{97}$Ru, $^{111}$In, $^{113m}$In, $^{67}$Ga, and $^{68}$Ga, with the proviso that when $R^2$ is —CH$_2$CO$_2$H or —CH$_2$CH$_2$CO$_2$H, then the radioactive metal ion is selected from the group consisting of $^{186}$Re, $^{188}$Re, $^{99m}$Tc, $^{111}$In, $^{113m}$In, $^{67}$Ga, and $^{68}$Ga; and
covalently attached to a protein or an antibody or antibody fragment; and
a physiologically acceptable carrier.

17. A pharmaceutical formulation of claim 16 wherein:
m and n are 2 or 3;

R² is hydrogen;
R¹ is

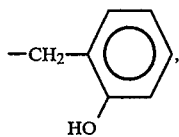,

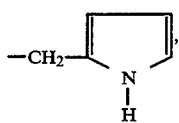, or

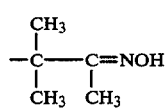

Y is amino or isothiocyanato; or
a pharmaceutically acceptable salt thereof.

18. A formulation of claim 16 which is the conjugate of $^{105}$Rh with bis(2-hydroxybenzyl)-4-(p-aminobenzyl)-diethylenetriamine to IgG and a pharmaceutically acceptable carrier.

19. A formulation of claim 16 which is the complex of $^{99m}$Tc with bis(2-hydroxybenzyl)-4-(p-aminobenzyl)-diethylenetriamine to IgG and a pharmaceutically acceptable carrier.

20. A formulation of claim 16 which is the complex of $^{57}$Co with bis(2-hydroxybenzyl)-4-(p-aminobenzyl)diethylenetriamine to IgG and a pharmaceutically acceptable carrier.

21. A formulation of claim 16 which is the complex of $^{105}$Rh with 1,7-bis(2-methylenepyrrole)-4-(p-aminobenzyl)diethylenetriamine to IgG and a pharmaceutically acceptable carrier.

22. A formulation of claim 16 which is the complex of $^{99m}$Tc with 2,2,12,12-tetramethyl-4,7,10-triaza-7-(p-aminobenzyl)-1,13-tridecane dithiol to IgG and a pharmaceutically acceptable carrier.

* * * * *